(12) United States Patent
Stumbaugh et al.

(10) Patent No.: US 12,359,241 B2
(45) Date of Patent: Jul. 15, 2025

(54) COAGULOGEN-FREE CLARIFIED LIMULUS AMEBOCYTE LYSATE

(71) Applicant: LONZA WALKERSVILLE, INC., Walkersville, MD (US)

(72) Inventors: Candice Stumbaugh, Chambersburg, PA (US); Leben Tadesse, Gaithersburg, MD (US); Karen Lin, Potomac, MD (US)

(73) Assignee: LONZA WALKERSVILLE, INC., Walkersville, MD (US)

( * ) Notice: Subject to any disclaimer, the term of this patent is extended or adjusted under 35 U.S.C. 154(b) by 0 days.

(21) Appl. No.: 17/737,578

(22) Filed: May 5, 2022

(65) Prior Publication Data
US 2022/0267824 A1    Aug. 25, 2022

Related U.S. Application Data

(62) Division of application No. 15/868,318, filed on Jan. 11, 2018, now Pat. No. 11,352,656.

(60) Provisional application No. 62/445,136, filed on Jan. 11, 2017.

(51) Int. Cl.
*G01N 33/579*    (2006.01)
*C12Q 1/37*    (2006.01)

(52) U.S. Cl.
CPC ............. *C12Q 1/37* (2013.01); *G01N 33/579* (2013.01); *G01N 2400/50* (2013.01)

(58) Field of Classification Search
CPC .......................... G01N 33/579; G01N 2400/50
See application file for complete search history.

(56) References Cited

U.S. PATENT DOCUMENTS

| | | | |
|---|---|---|---|
| 5,208,148 A | 5/1993 | Haugland et al. | |
| 5,242,805 A | 9/1993 | Naleway et al. | |
| 5,310,657 A | 5/1994 | Berzofsky | |
| 5,362,628 A | 11/1994 | Haugland et al. | |
| 5,576,424 A | 11/1996 | Mao et al. | |
| 5,695,948 A | 12/1997 | Tanaka et al. | |
| 5,773,236 A | 6/1998 | Diwu et al. | |
| 5,830,912 A | 11/1998 | Gee et al. | |
| 7,846,678 B2 | 12/2010 | Pepe et al. | |
| 11,156,614 B2 | 10/2021 | Stumbaugh et al. | |
| 2010/0203071 A1 | 8/2010 | Blais et al. | |
| 2018/0038864 A1 | 2/2018 | Stumbaugh et al. | |
| 2022/0074940 A1 | 3/2022 | Stumbaugh et al. | |

FOREIGN PATENT DOCUMENTS

| | | |
|---|---|---|
| CN | 102305788 A | 1/2012 |
| CN | 104155442 A | 11/2014 |
| EP | 0507952 A1 | 10/1992 |
| EP | 0426395 B1 | 1/1997 |
| JP | 2014-014375 A | 1/2014 |
| WO | 2012/057609 A1 | 5/2012 |
| WO | 2018/026941 A1 | 2/2018 |
| WO | 2018/132562 A1 | 7/2018 |
| WO | 2019/006000 A1 | 1/2019 |

OTHER PUBLICATIONS

Brawner et al., "Heat pretreatment eliminates spurious butyrylcholinesterase enhancement of endotoxin levels in the kinetic chromogenic assay," Chemico-Biological Interactions 249:19-22 (2016).
International Search Report issued in international application No. PCT/US2018/013310, dated Mar. 28, 2018.
International Search Report issued in international application No. PCT/US2017/045137, dated Jan. 17, 2018.
Non-final Office Action issued in U.S. Appl. No. 15/668,101, dated Dec. 10, 2018.
Final Office Action issued in U.S. Appl. No. 15/668,101, dated Jun. 20, 2019.
Advisory Action issued in U.S. Appl. No. 15/668,101, dated Sep. 4, 2019.
Advisory Action issued in U.S. Appl. No. 15/668,101, dated Oct. 25, 2019.
Non-final Office Action issued in U.S. Appl. No. 15/668,101, dated Aug. 18, 2020.
Final Office Action issued in U.S. Appl. No. 15/668,101, dated Feb. 26, 2021.
Advisory Action issued in U.S. Appl. No. 15/668,101, dated Jun. 18, 2021.
Notice of Allowance issued in U.S. Appl. No. 15/668,101, dated Jul. 30, 2021.
Corrected Notice of Allowance issued in U.S. Appl. No. 15/668,101, dated Aug. 12, 2021.
Corrected Notice of Allowance issued in U.S. Appl. No. 15/668,101, dated Sep. 9, 2021.
Aisimo Corp., "What is a Kilodalton?" 2009, retrieved online at http://www.aisimo.org/faq/membrane-filter/85.php.
Chromogenix, S-2423 Data Sheet, created on Nov. 6, 1997, retrieved online at http://www.chromogenicsubstrates.com/downloads/chromogenic_substrates_s2423.pdf.
Du Moulin et al., "Detection of Gram-Negative Bacteremia by Limulus Amebocyte Lysate Assay: Evaluation in a Rat Model of Peritonitis," J Infect Dis 151(1):148-152 (1985).

(Continued)

*Primary Examiner* — Sharmila G Landau
*Assistant Examiner* — Paul C Martin
(74) *Attorney, Agent, or Firm* — Medler Ferro Woodhouse & Mills PLLC

(57) ABSTRACT

The present invention is related to compositions comprising clarified limulus amebocyte lysate (LAL), wherein the LAL is substantially free of coagulogen and methods of making such compositions. The invention further relates to a method of detecting an endotoxin in a sample using a chromogenic assay, the method comprising: (a) contacting the sample with a reagent comprising clarified LAL and a chromogenic substrate; and (b) measuring a chromogenic effect resulting from a change in the chromogenic substrate in the presence of endotoxin in the sample, wherein the LAL is substantially free of coagulogen. The invention also relates to kits comprising clarified LAL substantially free of coagulogen, and methods of making such.

20 Claims, 19 Drawing Sheets

(56) References Cited

OTHER PUBLICATIONS

Harada-Suzuki et al., Further Studies on the Chromogenic Substrate Assay Method for Bacterial Endotoxins Using Horseshoe Crab (*Tachypleus tridentatus*) Hemocyte Lysate, J Biochem 92:793-800 (1982).

Hurley, "Endotoxemia: Methods of detection and clinical correlates," Clinical Microbiology Reviews 8(2):268-292 (1995).

"LAL Reagent Products for Detection of Bacterial Endotoxin; PYROSTAR", Wako Chemicals, pp. 1-14 (2014), retrieved online at https://5.imimg.com/data5/AY/HF/MY-819970/bacterial-endotoxin-test-kit.pdf.

Lindsay et al., "Single-Step, Chromogenic Limulus Amebocyte Lysate Assay for Endotoxin," Journal of Clinical Microbiology 27(5):947-951 (1989).

Miyata et al., "The Amino Acid Sequence of Coagulogen Isolated from Southeast Asian Horseshoe Crab, Tachypeus gigas," J. Biochem. 95(6):1793-1801 (1984).

Nachum et al., "Chromogenic Limulus Amebocyte Lysate Assay for Rapid Detection of Gram-Negative Bacteriuria," J. Clin. Microbial. 21 (5):759-763 (1985).

Nakamura et al., "Fractionation of Limulus amebocyte lysate—Characterization of activation of the proclotting enzyme by an endotoxin-mediated activator," Biochimica et Biophysica Acta 707(2):217-225 (1982).

Novitsky, "Limulus amebocyte lysate (LAL) detection of endotoxin in human blood," Journal of Endotoxin Research 1(4): 253-263 (1994).

Obayashi et al., "A new chromogenic endotoxin-specific assay using recombined limulus coagulation enzymes and its clinical applications," Clinica Chimica Acta 149:55-65 (1985).

"Pyrochrome for the Detection and Quantification of Gram Negative Bacterial Endotoxins (Lipopolysaccharides)," Associates of Cape Cod Incorporated, Jan. 2011, retrieved online at https://www.acciusa.com/pdfs/accProduct/Pyrochrome_multilang_IFUs/PyrochromeIFU_PN000856_en_r3.pdf.

"PyroGene Recombinant Factor C Endotoxin Detection Assay," Product Insert, Lonza Pharma & Biotech (2012).

Srimal et al., "The Complete Amino Acid Sequence of Coagulogen Isolated from Southeast Asian Horseshoe Crab, *Carcinoscorpius rotundicauda*," J. Biochem. 98(2):305-318 (1985).

Torano et al., "Properties of the Clotting Enzyme Responsible for Endotoxin-Mediated Limulus Coagulation," Thrombosis Research 34(5):407-417 (1984).

Non-Final Office Action issued in U.S. Appl. No. 17/482,918, dated May 18, 2023.

Notice of Allowance issued in U.S. Appl. No. 17/482,918, dated Oct. 18, 2023.

Iwanaga et al., "Evolution and phylogeny of defense molecules associated with innate immunity in horseshoe crab." Front Biosci 3(4): D973-D984 (1998).

Iwanaga, "Biochemical principle of Limulus test for detecting bacterial endotoxins." Proceedings of the Japan Academy, Series B 83(4): 110-119 (2007).

Miyata et al., "The amino acid sequence of coagulogen isolated from southeast Asian horseshoe crab, Tachypleus gigas." The Journal of Biochemistry 95(6): 1793-1801 (1984).

Srimal et al., "The complete amino acid sequence of coagulogen isolated from Southeast Asian NPL4 horseshoe crab, *Carcinoscorpius rotundicauda*." The Journal of Biochemistry 98(2): 305-318 (1985).

| 50mOD | | BLANK | 0.005EU/ml | Sepa. 0-0.005EU/ml | 0.005EU/ml rxn. TIME (MINS) |
|---|---|---|---|---|---|
| A) | 50/80/20, 0.020%Z314, 1yoLAL SOURCE | 5515 | 1497 | 4018 | 25 |
| B) | 50/80/20, 0.020%Z314, 2yoLAL SOURCE | 6310 | 1558 | 4752 | 26 |
| C) | 50/80/20, 0.020%Z314, 3yoLAL SOURCE | 6915 | 1685 | 5230 | 28 |

| 30mOD | | BLANK | 0.005EU/ml | Sepa. 0-0.005EU/ml | 0.005EU/ml rxn. TIME (MINS) |
|---|---|---|---|---|---|
| A) | 50/80/20, 0.020%Z314, 1yoLAL SOURCE | 3675 | 1220 | 2455 | 20 |
| B) | 50/80/20, 0.020%Z314, 2yoLAL SOURCE | 4330 | 1275 | 3055 | 21 |
| C) | 50/80/20, 0.020%Z314, 3yoLAL SOURCE | 4005 | 1300 | 2705 | 22 |

| 20mOD | | BLANK | 0.005EU/ml | Sepa. 0-0.005EU/ml | 0.005EU/ml rxn. TIME (MINS) |
|---|---|---|---|---|---|
| A) | 50/80/20, 0.020%Z314, 1yoLAL SOURCE | 2705 | 1045 | 1660 | 17 |
| B) | 50/80/20, 0.020%Z314, 2yoLAL SOURCE | 3220 | 1075 | 2145 | 18 |
| C) | 50/80/20, 0.020%Z314, 3yoLAL SOURCE | 2655 | 1035 | 1620 | 17 |

FIG. 6

| PROTEINS & PEPTIDES | MASS (kDa) | FUNCTION/SPECIFICITY | LOCALIZATION |
|---|---|---|---|
| COAGULATION FACTORS | | | |
| FACTOR C | 123 | SERINE PROTEASE | L-GRANULE |
| FACTOR B | 64 | SERINE PROTEASE | ND |
| FACTOR G | 110 | SERINE PROTEASE | L-GRANULE |
| PROCLOTTING ENZYME | 54 | SERINE PROTEASE | L-GRANULE |
| COAGULOGEN | 20 | GELATION | L-GRANULE |
| PROTEASE INHIBITORS | | | |
| LICI-1 | 48 | SERPIN/FACTOR C | L-GRANULE |
| LICI-2 | 42 | SERPIN/CLOTTING ENZYME | L-GRANULE |
| LICI-3 | 53 | SERPIN/FACTOR G | L-GRANULE |
| TRYPSIN INHIBITOR | 6.8 | KUNITZ-TYPE | ND |
| LTI | 16 | NEW TYPE | ND |
| LEBP-PI | 12 | NEW TYPE | L-GRANULE |
| LINNULUS CYSTATIN | 12.6 | CYSTATIN FAMILY 2 | L-GRANULE |
| α2-MACROGLOBULIN | 180 | COMPLEMENT | PLASMA |
| ANTIMICROBIAL SUBSTANCES | | | |
| ANTI-LPS FACTOR | 12 | GNB | L-GRANULE |
| TACHYPLESINS | 2.3 | GNB, GPB, FN | S-GRANULE |
| POLYPHEMUSINS | 2.3 | GNB, GPB, FN | S-GRANULE |
| BIG DEFENSIN | 8.6 | GNB, GPB, FN | L & S-GRANULES |
| TACHYCITIN | 8.3 | GNB, GPB, FN | S-GRANULE |
| TACHYSTATINS | 6.5 | GNB, GPB, FN | S-GRANULE |
| FACTOR D | 42 | GNB | L-GRANULE |
| LECTINS | | | |
| TACHYLECTIN-1 | 27 | LPS (KDO), LTA | L-GRANULE |
| TACHYLECTIN-2 | 27 | GkNAc, LTA | L-GRANULE |
| TACHYLECTIN-3 | 15 | LPS | L-GRANULE |
| TACHYLECTIN-4 | 470 | LPS (O-ANTIGEN), LTA | ND |
| TACHYLECTIN-5 | 380-440 | N-ACETYL GROUP | ND |
| LINNUNECTIN | 54 | PC | L-GRANULE |
| 18K-LAF | 18 | HEMOCYTE AGGREGATION | L-GRANULE |
| LINNULUN | 300 | HLA/PC, PE, SA, KDO | PLASMA |
| LCRP | 300 | PC, PE | PLASMA |
| TCRP-1 | 300 | PE | PLASMA |
| TCRP-2 | 330 | HLA/PE, SA | PLASMA |
| TCRP-3 | 340 | HLA/SA, KDO | PLASMA |
| POLYPHEMIN | ND | LTA, GlcNAc | PLASMA |
| TTA | ND | SA, GkNAc, GalNAc | PLASMA |
| LIPHEMIN | 400-500 | SA | HEMOLYMPH |
| CARCINOSCORPIN | 420 | SA, KDO | HEMOLYMPH |
| OTHERS | | | |
| TRANSGLUTAMINASE | 86 | CROSS-LINKING | CYTOSOL |
| 8.6 kDa PROTEIN | 8.6 | TGASE SUBSTRATE | L-GRANULE |
| PRO-RICH PROTEIN | 80 | TGASE SUBSTRATE | L-GRANULE |
| LINNULUS KEXIN | 70 | PRECURSOR PROCESSING | ND |
| L1 | 11 | UNKNOWN | L-GRANULE |
| L4 | 11 | UNKNOWN | L-GRANULE |

FIG. 14

COAGULOGEN-FREE CLARIFIED LIMULUS AMEBOCYTE LYSATE

CROSS-REFERENCE TO REPLATED APPLICATIONS

The present application is a division of U.S. application Ser. No. 15/868,318, filed Jan. 11, 2018, now patented as U.S. Pat. No. 11,352,656 on Jun. 7, 2022, which claims priority to U.S. Provisional Application No. 62/445,136, filed Jan. 11, 2017, the disclosures of each of which are incorporated by reference herein in their entireties.

FIELD OF THE INVENTION

The present invention is related to a composition comprising clarified limulus amebocyte lysate (LAL), wherein the LAL is substantially free of coagulogen, and methods of making the composition. The invention further relates to a method of detecting an endotoxin in a sample using a chromogenic assay, the method comprising: (a) contacting the sample with a reagent comprising clarified LAL and a chromogenic substrate; and (b) measuring a chromogenic effect resulting from a change in the chromogenic substrate in the presence of endotoxin in the sample, wherein the LAL is substantially free of coagulogen. The invention also relates to kits comprising clarified LAL substantially free of coagulogen, and methods of making such.

BACKGROUND OF THE INVENTION

Gram negative bacterial endotoxin is a biological pyrogen that causes fever when introduced intravenously. The endotoxin, also known as lipopolysaccharide (LPS), is found in the outer membrane of Gram-negative bacteria, such as *Salmonella, Escherichia coli, Shigella* and *Neisseria*. The toxicity mechanism the endotoxins trigger is reported to be caused by the lipid fraction of the lipopolysaccharides. For example, when the lysis of the bacteria within an organism occurs, the response to the lipids introduced into the bloodstream can be through the activation of the complement system. This lipid fraction leads to the release of different cytokines, such as interleukins 1 and 8. The production of the tumor necrosis factor may also be activated. The infection produced is associated with inflammatory processes and can pose a great danger for the infected organism. Interleukin 1 is a family of cytokines that the organism releases as an immune response and against the inflammation. This response leads to the migration of neutrophils towards the place where the infection has occurred, producing chemotaxis. This facilitates the occurrence of phagocytosis; however, in some cases, depending on the state of the immune system of the individual and the level of infection, the endotoxin could lead to generalized sepsis, along with the risks that are brought about by the sepsis. Many cases have been reported where Gram-negative bacteria have caused multiple organ failure and even death by systemic infection in higher mammals. Due to the adverse effects associated with endotoxins, early and sensitive detection of endotoxin is critical for the pharmaceutical industry and healthcare community.

The Limulus Amebocyte Lysate (LAL) test was commercially introduced in the 1970s to detect endotoxins. LAL is derived from blood cells, or amebocytes, of the horseshoe crab, *Limulus polyphemus*. The original LAL test constituted a cascade of serine proteases which are triggered by trace levels of endotoxin, culminating in a gel clot at the end of the reaction. Factor C, which normally exists as a zymogen, is the primer of this coagulation cascade. In vivo, Factor C is the perfect biosensor, which alerts the horseshoe crab of the presence of a Gram-negative invader. The hemostatic end-point entraps the invader, killing it and limiting further infection.

The LAL test can be modified to use different methods to measure the response of the amebocytes against the endotoxins. These methods include the so-called Gel-Clot method, turbidimetric and chromogenic methods. These LAL tests are recommended in international pharmacopoeias as the method for detecting bacterial toxins both in the raw materials used to produce medicines and for the final products. These tests are also useful for the cosmetics industry and in food production as it is the method recommended by the FDA (Food and Drug Administration) for the detection of pyrogens.

BRIEF SUMMARY OF THE INVENTION

Provided herein are compositions comprising clarified limulus amebocyte lysate (LAL), wherein the composition is substantially free of coagulogen. In embodiments, the compositions comprising clarified LAL further comprise a buffer and a detergent. In embodiments, the compositions comprise 50% clarified LAL.

In embodiments, the invention provides compositions comprising (a) clarified LAL, wherein the composition is substantially free of coagulogen, and (b) a chromogenic substrate.

Embodiments herein are further directed to compositions comprising the clarified LAL, a buffer, a detergent, and a chromogenic substrate, wherein the composition comprises 30% to 50% LAL (v/v) and 10% to 30% (v/v) chromogenic substrate.

In embodiments, the invention further provides compositions comprising clarified LAL, wherein the composition is substantially free of coagulogen, wherein the composition is made by a method comprising: (a) centrifuging a solution derived from lysed amebocytes from *Limulus polyphemus* at 2,000 rpm for 8 minutes at 4° C. to produce a supernatant; (b) combining the supernatant from (a) with a buffer; (c) subjecting the combination from (b) to tangential flow filtration using a 30 kDa membrane filter to produce a retentate; and (d) centrifuging the retentate from (c) at 5,000 rpm for 5 minutes at 4° C. to produce a supernatant, wherein the supernatant is clarified LAL that is substantially free of coagulogen.

In embodiments, the invention further provides compositions comprising clarified LAL, wherein the composition is substantially free of coagulogen, wherein the composition is made by a method comprising: (a) obtaining a solution derived from lysed amebocytes from *Limulus polyphemus*; combining the solution from (a) with a buffer; (b) combining the solution from (a) with buffer; (c) subjecting the combination from (b) to continuous tangential flow filtration using a 20 kDa to 50 kDa membrane filter to produce a retentate; and (d) centrifuging the retentate from (c) at greater than 20,000×g for greater than 25 minutes to produce a supernatant, wherein the supernatant is clarified LAL that is substantially free of coagulogen. In some embodiments, the continuous TFF of (c) comprises at least four diafiltration volumes. In some embodiments, the continuous TFF of (c) comprises at least six diafiltration volumes.

Embodiments herein are directed to a method of detecting an endotoxin in a sample using a chromogenic assay, the method comprising: (a) contacting the sample with a reagent comprising clarified limulus amebocyte lysate (LAL) and a chromogenic substrate; and (b) measuring a chromogenic effect resulting from a change in the chromogenic substrate in the presence of endotoxin in the sample, wherein the LAL is substantially free of coagulogen.

In some embodiments, the chromogenic substrate is a p-nitroaniline covalently bonded to a greater than three amino acids. In some embodiments, the chromogenic substrate is Ac-Ile-Glu-Ala-Arg-pNA. In some embodiments, the change in the chromogenic substrate occurs due to an enzymatic reaction. In some embodiments, the enzymatic reaction is cleavage of a chromophore from a polypeptide. In some embodiments, the chromogenic effect is measured by detecting at absorbance at 380 nm-420 nm. In some embodiments, chromogenic effect is measured by detecting absorbance at 405 nm.

In some embodiments, the reagent is a liquid. In some embodiments, the reagent is an aqueous liquid. In some embodiments, the reagent is lyophilized and then reconstituted in an aqueous liquid prior to contacting with the sample.

In some embodiments, the LAL is lyophilized, and then reconstituted prior to contacting with the sample. In some embodiments, the LAL is frozen, and then thawed prior to contacting with the sample. In some embodiments, the chromogenic substrate is lyophilized, and then reconstituted prior to contacting with the sample.

In some embodiments, the sample is a biological sample. In some embodiments, the sample is selected from the group consisting of a parenteral dosage form, vaccine, antibiotic, therapeutic protein, therapeutic nucleic acid, therapeutic antibody, and biological product. In some embodiments, the clarified LAL substantially free of coagulogen has less than 5% (wt/wt) of coagulogen relative to total protein in the LAL as measured by SDS-PAGE and confirmed by Western blot. In some embodiments, the clarified LAL substantially free of coagulogen has less than 2% (wt/wt) of coagulogen relative to total protein in the LAL. In some embodiments, the clarified LAL substantially free of coagulogen has less than 0.5% (wt/wt) of coagulogen relative to total protein in the LAL.

In some embodiments, the clarified LAL substantially free of coagulogen has a concentration of coagulogen at less than 5 µg/µL. In some embodiments, the clarified LAL substantially free of coagulogen has a concentration of coagulogen at less than 3 µg/µL. In some embodiments, the clarified LAL substantially free of coagulogen has a concentration of coagulogen at less than 2 µg/µL. In some embodiments, the chromogenic assay is conducted using single cuvette spectroscopy, multiple cuvette spectroscopy, or a microplate reader.

In some embodiments, the method further comprises comparing the chromogenic effect to a standard to determine the quantity of endotoxin in the sample.

In some embodiments, the disclosure is directed to a method of detecting an endotoxin in a biological sample using a chromogenic assay, the method comprising: (a) contacting the biological sample with an aqueous reagent comprising clarified limulus amebocyte lysate (LAL) and Ac-Ile-Glu-Ala-Arg-pNA; (b) measuring the change in absorbance at 405 nm resulting from the enzymatic cleavage of pNA from Ac-Ile-Glu-Ala-Arg-pNA in the presence of endotoxin in the sample; wherein the LAL is substantially free of coagulogen.

In some embodiments, the method of the present disclosure has increased sensitivity. In some embodiments, the method has a sensitivity of <0.001 EU/mL endotoxin.

In some embodiments, the method of the present disclosure is directed to a kit comprising: (a) clarified limulus amebocyte lysate (LAL), wherein the LAL is substantially free of coagulogen; (b) a chromogenic substrate; and (c) instructions for detecting an endotoxin using the LAL and chromogenic substrate.

In some embodiments, the clarified LAL is lyophilized. In some embodiments, the clarified LAL is in an aqueous solution. In some embodiments, the LAL and the chromogenic substrate are in a single container. In some embodiments, the kit further comprises a sterile container comprising the clarified LAL. In some embodiments, the sterile container is a sterile vial. In some embodiments, the kit further comprises a control standard endotoxin.

In some embodiments, the disclosure is directed to a method of making clarified limulus amebocyte lysate (LAL) substantially free of coagulogen, the method comprising centrifuging a solution derived from lysed amebocytes from *Limulus polyphemus* at 1000 to 3000 rpm for 2 to 15 minutes at 2 to 10° C. to produce a supernatant; combining the supernatant from (a) with a buffer; filtering the combination from (b) using a 20 kDa to 50 kDa filter to produce a retentate; centrifuging the retentate from (c) at 3000 to 7000 rpm for 2 to 10 minutes at 2 to 10° C. to produce a supernatant, wherein the supernatant comprises clarified LAL that is substantially free of coagulogen.

In some embodiments, the filter is tangential flow filtration (TFF). In some embodiments, the TFF filter is a modified polyethersulfone (mPES) membrane filter. In some embodiments, the TFF is performed at a flow rate of 350 mL/min to 500 mL/min. In some embodiments, the buffer is a Tris buffer or IVIES buffer. In some embodiments, the buffer has a pH of about 7.0 to 8.0.

In some embodiments, the disclosure is directed to a method of making clarified limulus amebocyte lysate (LAL) substantially free of coagulogen, the method comprising: (a) obtaining a solution derived from lysed amebocytes from *Limulus polyphemus*; (b) combining the solution from (a) with a buffer; (c) subjecting the combination from (b) to continuous tangential flow filtration (TFF) using a 20 kDa to 50 kDa membrane filter to produce a retentate; and (d) centrifuging the retentate from (c) at greater than 20,000×g for greater than 25 minutes to produce a supernatant, wherein the supernatant is clarified LAL that is substantially free of coagulogen. In some embodiments, the solution in (a) comprises a supernatant obtained from centrifuging lysed amebocytes from *Limulus polyphemus* at 1000 to 3000 rpm for 2 to 15 minutes at 2 to 10° C. In some embodiments, the centrifuging in (a) comprises centrifuging at 2000 rpm. In some embodiments, the centrifuging in (a) comprises centrifuging for 8 minutes.

In some embodiments, the centrifuging comprises centrifuging at 2 to 10° C., e.g., 4° C. In some embodiments, the continuous TFF of (c) comprises at least four diafiltration volumes. In some embodiments, the continuous TFF of (c) comprises at least six diafiltration volumes. In some embodiments, the centrifuging of (d) comprises centrifuging at 40,000×g. In some embodiments, the centrifuging of (d) comprises centrifuging for 30 minutes. In some embodiments, the buffer is a Tris buffer or MES buffer. In some embodiments, the buffer has a pH of about 7.0 to 8.0.

BRIEF DESCRIPTION OF DRAWINGS

The foregoing and other features and aspects of the present technology can be better understood from the following description of embodiments and as illustrated in the accompanying drawings. The accompanying drawings, which are incorporated herein and form a part of the specification, further serve to illustrate the principles of the present technology.

FIG. 6: Table of reaction parameters for clarified LAL substantially free of coagulogen for 1 year old, 2 year old and 3 year old LAL sources in formulations containing 40% (v/v) clarified coagulogen-free LAL and 20% chromogenic substrate (50/80/20 formulation).

FIG. 14: Table showing known proteins and peptides present in LAL. Highlighted proteins and peptides have a molecular weight of less than 30 kDa and can be removed with a 30 kDa molecular weight cut-off filter. Reproduced from Iwanga and Kawabata, *Frontiers in Bioscience* 3: d973-984 (1998).

DETAILED DESCRIPTION OF THE INVENTION

Figure 1:
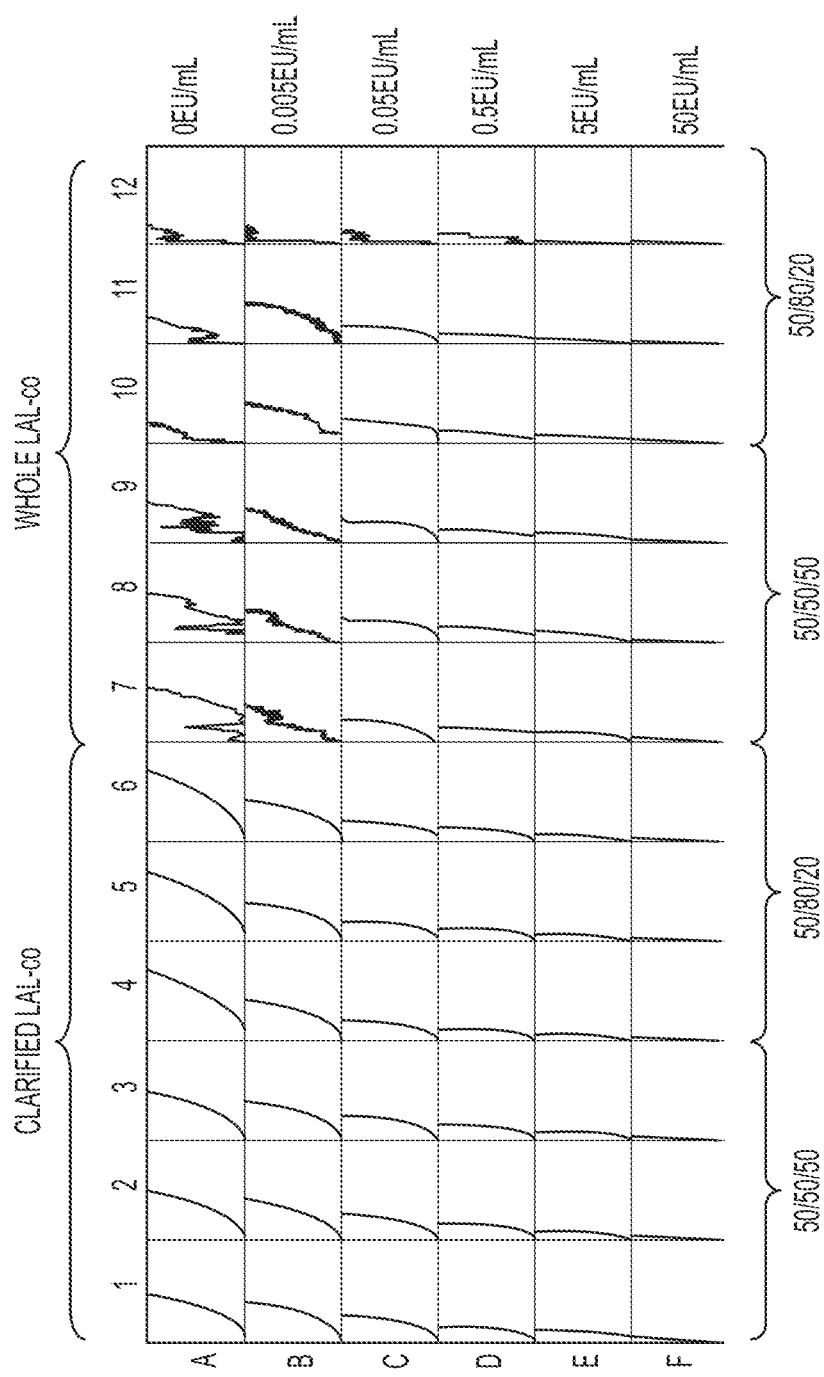
FIG. 1: Reaction profiles of formulations comprising clarified LAL substantially free of coagulogen ("LAL-co") (samples 1-6) and unclarified LAL-co (samples 7-12), at either a 50/50/50 formulation, or a 50/80/20 formulations. See Example 1.

It should be appreciated that the implementations shown and described herein are examples and are not intended to otherwise limit the scope of the application in any way.

The published patents, patent applications, websites, company names, and scientific literature referred to herein are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

As used in this specification, the singular forms "a," "an" and "the" specifically also encompass the plural forms of the terms to which they refer, unless the content clearly dictates otherwise. The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

Technical and scientific terms used herein have the meaning commonly understood by one of skill in the art to which the present application pertains, unless otherwise defined. Reference is made herein to various methodologies and materials known to those of skill in the art. The disclosures of any documents cited herein is incorporated by reference herein in their entireties.

In some embodiments, the invention is directed to methods of detecting an endotoxin. The term "endotoxin" generally refers to the lipopolysaccharide complex associated with the outer membrane of gram-negative bacteria. The term "endotoxin" is occasionally used to refer to any cell-associated bacterial toxin. While endotoxin refers to cell associated lipopolysaccharides, exotoxin refers to toxins secreted by bacteria and are predominantly polypeptides in nature.

The biological activity of endotoxin is associated with the lipopolysaccharide (LPS). Lipopolysaccharides are part of the outer membrane of the cell wall of gram-negative bacteria. Lipopolysaccharides are invariably associated with gram-negative bacteria whether the organisms are pathogenic or not. Toxicity is associated with the lipid component (Lipid A) and immunogenicity is associated with the polysaccharide components. The cell wall antigens (O antigens) of gram-negative bacteria are the polysaccharide components of LPS. In addition, LPS can elicit a variety of inflammatory responses in an animal.

Gram-negative bacteria, within animals, can release minute amounts of endotoxin while growing. This may result in the stimulation of natural immunity. It is known that small amounts of endotoxin may be released in a soluble form by young cultures grown in the laboratory. But for the most part, endotoxins remain associated with the cell wall until disintegration of the organisms. Disintegration of the bacterial organisms can result from autolysis, external lysis mediated by complement and lysozyme, and phagocytic digestion of bacterial cells. Bacterial endotoxin is abundant in the human gut. Elevated concentrations of endotoxins are associated with a number of conditions including some metabolic syndrome diseases. Metabolic syndrome diseases include, for example, atherosclerosis, insulin resistance, diabetes mellitus, and obesity. Increased endotoxin levels have also been associated with fatty liver disease and Crohn's disease. Endotoxin may also leak out of the GI tract when present at elevated levels. Endotoxin is a potent inflammatory antigen and leaking of the endotoxin can result in systemic inflammatory response.

Compared to the classic exotoxins of bacteria, endotoxins are less potent and less specific in their action, since they do not act enzymatically. Endotoxins are heat stable (boiling for 30 minutes does not destabilize endotoxin), but certain powerful oxidizing agents such as superoxide, peroxide and hypochlorite, have been reported to neutralize them. Since these are powerful oxidizing agents they are not particularly amenable to a therapeutic composition for neutralizing endotoxins.

The endotoxins of the present invention can originate from Gram-negative bacteria. Exemplary Gram-negative bacteria include, but are not limited to, *Escherichia* spp., *Shigella* spp., *Salmonella* spp., *Campylobacter* spp., *Neisseria* spp., *Haemophilus* spp., *Aeromonas* spp., *Francisella* spp., *Yersinia* spp., *Klebsiella* spp., *Bordetella* spp., *Legionella* spp., Corynebacteria spp., *Citrobacter* spp., *Chlamydia* spp., *Brucella* spp., *Pseudomonas* spp., *Helicobacter* spp. and *Vibrio* spp. Gram negative bacteria also may be those that fall in the Enterobacteriaceae, Pseudomonadaceae, Neisseriaceae, Veillonellaceae, Bacteroidaceae, Vibrionaceae, Pasteurellaceae, and Fusobacteriaceae families. In some embodiments, the endotoxin is from *Salmonella* or *Escherichia* spp.

As used herein, the term "endotoxin activity" refers to portions of Gram-negative bacteria that can cause toxicity, including pyrogenicity and septic shock. The toxic effects attributed to endotoxin have been found to be associated with the glycosylated lipid A portion of a lipopolysaccharide molecule present in or derived from the outer membrane of Gram-negative bacteria.

The term "Lipopolysaccharide" (LPS) refers to large molecules consisting of a lipid and a polysaccharide (glycophospholipid) joined by a covalent bond. LPS comprises three parts: 1) 0 antigen; 2) Core oligosaccharide, and 3) Lipid A. The 0-antigen is a repetitive glycan polymer attached to the core oligosaccharide, and comprises the outermost domain of the LPS molecule. Core oligosaccharide attaches directly to lipid A and commonly contains sugars such as heptose and 3-deoxy-D-mannooctulosonic acid (also known as KDO, keto-deoxyoctulosonate). Lipid A is a phosphorylated glucosamine disaccharide linked to multiple fatty acids. The fatty acids anchor the LPS into the bacterial membrane, and the rest of the LPS projects from the cell surface. Bacterial death may result if LPS is mutated or removed.

Endotoxin activity resides in the lipid A domain portion of LPS. When bacterial cells are lysed by the immune system, fragments of membrane containing lipid A are released into the circulation, causing fever (pyrogenicity), diarrhea, and a potentially fatal shock (called endotoxic or septic shock). Toxicity of LPS is expressed by lipid A through the interaction with B-cells and macrophages of the mammalian immune system, a process leading to the secretion of proinflammatory cytokines, mainly tumor necrosis factor (TNF), which may have fatal consequences for the host. Lipid A also activates human T-lymphocytes (Th-1) "in vitro" as well as murine CD4+ and CD8+ T-cells "in vivo", a property which allows the host's immune system to mount a specific, anamnestic IgG antibody response to the variable-size carbohydrate chain of LPS. On these bases, LPS has been recently recognized as a T-cell dependent antigen "in vivo". Thus, in some embodiments, the method of the present invention is directed to detecting Lipid A.

In some embodiments, the endotoxin is detected using a chromogenic assay. As used herein, chromogenic assays measure or detects a change in absorbance in a chromogenic substrate (i.e., a chromogen) in the presence of an endotoxin. In some embodiments, the change in absorbance in the chromogenic substrate is due to enzyme activity. In some embodiments, the term "chromogenic substrate" refers to a substrate before and after enzymatic activity. For example, if the chromogenic substrate is a peptide-chromophore which is cleaved by an enzyme to result in a peptide and a chromophore, the term "chromogenic substrate" would refer to the peptide-chromophore, the cleaved peptide, and the release chromophore. In some embodiments, synthetic chromogens can be used. In some embodiments, a naturally produced chromogen can be used. In some embodiments, the chromogenic substrate is a synthetic peptide. In some embodiments, the substrates are very sensitive, i.e. they can detect very low enzyme activities.

The ability of a reagent comprising a chromogenic substrate to detect low enzyme concentrations makes them useful in, for example, the search for the presence of certain enzyme activities associated with endotoxins, either in research or in quality control procedures. Sometimes there is a lack of correspondence between a natural (i.e., natural substrate for the enzyme) and a synthetic chromogenic substrate in their responses to a certain enzyme preparation. In some embodiments, a chromogenic substrate is less selective, i.e. it has less discrimination in its reactivity towards related enzymes compared to the natural substrate.

The term "chromogenic substrate" refers to the substrate, e.g., compound or polypeptide, in the assay that changes its absorbance spectra, e.g., a change in color, in the presence of the endotoxin. Chromogenic substrate refers to substrates that both (i) absorb, and/or (ii) do not absorb at a specified wavelength. Thus, e.g., according to the present disclosure, a chromogenic substrate may originally not absorb at a specified wavelength, (e.g., non-absorbing at visual wavelengths), and then in the presence of an endotoxin, may begin to absorb at the specified wavelengths (e.g., at visual wavelengths). Alternatively, e.g., a chromogenic substrate may originally absorb at a specified wavelength (e.g., absorb at visual wavelengths), and then in the presence of an endotoxin, may not absorb at the specified wavelength (e.g., not absorb at visual wavelengths). In some embodiments, the chromogenic substrate may absorb at a given wavelength in the absence of an endotoxin, and then absorb at a different wavelength in the presence of an endotoxin. The change in absorbance characteristics, i.e., chromogenic effect, at one or more specified wavelengths can be correlated with the presence of endotoxin.

In some embodiments, the chromogenic substrate is a chromogenic peptide substrate. In some embodiments, the chromogenic peptide substrate is initially colorless. In some embodiments, the chromogenic peptide substrate initially has a color, e.g., a color in the visual spectrum (approximately 390-700 nm). In some embodiments, when the chromogenic peptide substrate is cleaved by an enzyme, a color change can occur, e.g., a chromophore is release, causing a color change in the resulting product. In some embodiments, cleavage changes the optical properties of the product, which are different from those of the uncleaved substrate and which can be measured by means of spectrophotometry. Non-limiting examples of chromogenic groups which can be coupled to a peptide substrate are para-nitroaniline (pNA), 5-amino-2-nitrobenzoic acid (ANBA), 7-amino-4-methoxycoumarin (ANC), quinonylamide (QUA), dimethyl 5-aminoisophthalate (DPA) and their derivatives. Fluorogenic substrates include, without limitation, Z-Gly-Pro-Arg-AMC [Z=Benzyloxycarbonyl; AMC=7-amino-4-methylcoumarin], homovanillic acid, 4-hydroxy-3-methoxyphenylacetic acid, reduced phenoxazines, reduced benzothiazines, Amplex®, resorufin β-D-galactopyranoside, fluorescein digalactoside (FDG), fluorescein diglucuronide and their structural variants (U.S. Pat. Nos. 5,208,148; 5,242,805; 5,362,628; 5,576,424 and 5,773,236, incorporated by reference), 4-methylumbelliferyl β-D-galactopyranoside, carboxyumbelliferyl β-D-galactopyranoside and fluorinated coumarin β-D-galactopyranosides (U.S. Pat. No. 5,830,912, incorporated by reference).

A non-limiting chromogenic assay is an enzymatic activity assay based on the Factor C/Factor B cascade. Factor C, the first component in the cascade, is a protease zymogen that is activated by endotoxin binding. In some embodiments, the chromogenic assay uses a recombinant form of Factor C (rFC). In this pathway, Factor B is activated by Factor C. Factor B activates a pro-clotting enzyme into a clotting enzyme. In some embodiments, the pro-clotting enzyme effects a chromogenic change in a chromogenic substrate. In some embodiments, the chromogenic assay is an LAL assay, e.g., the Endpoint Chromogenic LAL Assays from Lonza.

In some embodiments, the chromogenic assay is an LAL assay, wherein the initial part of the LAL endotoxin reaction activates a proclotting enzyme, which in turn enzymatically cleaves p-nitroaniline (pNA) from a synthetic substrate, producing a yellow color.

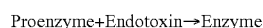

Proenzyme+Endotoxin→Enzyme

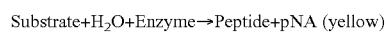

Substrate+H$_2$O+Enzyme→Peptide+pNA (yellow)

In some embodiments, gram-negative bacterial endotoxin can indirectly catalyze the activation of a proenzyme in the LAL. The initial rate of activation can be determined by the concentration of endotoxin present.

In some embodiments, the change in chromogenic substrate occurs due to an enzymatic reaction. In some embodiments, the enzymatic reaction results in cleavage of a peptide bond, thereby cleaving a chromophore substituent (e.g., p-NA) from a polypeptide. For example, the activated enzyme can catalyze the release of pNA from a colorless peptide substrate, e.g., Ac-lle-Glu-Ala-Arg-pNA. In some embodiments, the peptide substrate is a p-nitroaniline covalently bonded to greater than three amino acids. In some embodiments, embodiments, the chromogenic substrate is Ac-lle-Glu-Ala-Arg-pNA. In some embodiments, the chromogenic assay measures free pNA. In some embodiments, the chromogenic assay measures free pNA photometrically at an absorbance of 380 nm to 410 nm, e.g., 400 nm to 410 nm, or 405 nm. Methods of measuring absorbance are well known to those in the art. In some embodiments, the chromogenic assay is conducted using single cuvette spectroscopy, multiple cuvette spectroscopy, or a microplate reader to measure absorbance.

The free pNA can be measured photometrically at 380 nm to 410 nm, e.g., 405 nm, after the reaction is stopped with stop reagent. The concentration of endotoxin in a sample is calculated from a standard curve of absorbance values of solutions containing known amounts of an endotoxin standard.

One standard chromogenic assay for detecting endotoxin comprises contacting a sample with a reagent, wherein the reagent comprises limulus amebocyte lysate (LAL). In some embodiments, the reagent is a liquid, e.g., and aqueous liquid. Alternatively, the reagent can be lyophilized, and then reconstituted in an aqueous liquid, e.g., sterile water or buffer solution, prior to being contacted with the sample. In some embodiments, the reagent is a liquid. In some embodiments, the reagent is an aqueous liquid. In some embodiments, the reagent is lyophilized and then reconstituted in an aqueous liquid prior to contacting with the sample. In some embodiments, the LAL is lyophilized, and then reconstituted in the aqueous liquid prior to contacting with the sample. In some embodiments, the chromogenic substrate is lyophilized, and then reconstituted in an aqueous liquid prior to contacting with the sample. In some embodiments, lyophilization allows for a longer and/or more robust storage of the reagent, LAL, and or chromogenic substrate in the chromogenic assay. For example, in some embodiments, the lyophilized reagent, LAL and/or chromogenic substrate allows for greater than 20%, greater than 30%, greater than 40%, greater than 50%, greater than 60%, greater than 70%, greater than 80%, greater than 90% or greater than 100% increase in time of stability relative to a non-lyophilized reagent, LAL, and or chromogenic substrate in the chromogenic assay. "Stability" as used in this context refers to the assay functioning for its intended purpose, i.e., for detecting endotoxin at the same speed and sensitivity. For example, if a non-lyophilized reagent is stable for 3 weeks, a lyophilized reagent stable for 6 weeks would have a "100% increase" in time of stability.

In some embodiments, the LAL is frozen, and then thawed prior to contacting with the sample. In some embodiments, freezing the LAL allows for a longer and/or more robust storage of LAL. In some embodiments, the LAL that has been frozen and then thawed has the same or substantially the same assay performance as LAL that has not been frozen. "Same or substantially the same" assay performance in this context refers to a similar reduction in reaction time when comparing a blank reaction with a reaction using LAL. In some embodiments, the difference in reaction time reduction between LAL that has not been frozen and LAL that has been frozen and then thawed is less than 20%. In some embodiments, the difference in reaction time reduction is less than 10%. In some embodiments, the difference in reaction time reduction is less than 5%. In some embodiments, the difference in reaction time reduction is less than 1%. In some embodiments, the LAL is frozen and stored at about −20° C. In some embodiments, the LAL is frozen and stored at about −30, about −40, about −50, about −60, about −70, or about −80° C. In some embodiments, the LAL is flash frozen. In some embodiments, the LAL is flash frozen using dry ice or liquid nitrogen.

In some embodiments, the LAL is frozen for greater than one week, greater than 1 month, greater than 3 months, greater than 6 months, greater than 9 months, greater than 12 months, greater than 15 months, greater than 18 months, or greater than 24 months, after which the LAL that has been frozen is thawed and has same or substantially the same assay performance as LAL that was not been frozen. In some embodiments, the LAL is frozen for one week to five years, one month to four years, 3 months to three years, or 6 months to two years, after which the LAL that has been frozen is thawed and has same or substantially the same assay performance as LAL that was not been frozen.

The present disclosure provides for an improved method for detecting an endotoxin in a sample. The term "sample" can include any substance, compound, tool or instrument. However, for practical purposes, the sample can include a substance, compound, tool or instrument that has contact with a biological organism, e.g., a mammal, human, domesticated animal, or zoo animal. The term "sample" can refer to any medical device, pharmaceutical and biotech product in which sources of endotoxin (from raw material receipt through the end of the manufacturing process) may make the sample unsuitable for contact with cerebral spinal fluid or the cardiovascular system. In some embodiments, the term sample refers to a medical device which comes in contact with cerebral spinal fluid or cardiovascular system in vivo, e.g., with a human. In some embodiments, the term sample refers to a biological sample. In some embodiments, the sample is selected from the group consisting of a parenteral dosage form, vaccine, antibiotic, therapeutic protein, therapeutic nucleic acid, therapeutic antibody, and biological product.

The term "limulus amebocyte lysate" (LAL) refers to an aqueous extract of blood cells (amebocytes) from the horseshoe crab, *Limulus polyphemus*. The aqueous extract of blood cells from horseshoe crabs comprise coagulogen, a gel-forming protein of hemolymph that hinders the spread of invaders by immobilizing them. See, e.g., Iwanaga S, et al., *J. Biochem.* 98:305-318 (1985) and Iwanaga S, et al., *J. Biochem.* 95 (6): 1793-1801 (1984).

The clotting cascade system of the horseshoe crab (*Limulus*) is involved in both haemostasis and host defense. The cascade results in the conversion of coagulogen, a soluble protein, into an insoluble coagulin gel. The clotting enzyme excises the fragment peptide C from coagulogen, giving rise to aggregation of the monomers.

The term "coagulogen" refers to the polypeptide chain as found in Iwanaga (1984) and Iwanaga (1985), which is a single 175-residue polypeptide chain, that is cleaved after Arg-18 and Arg-46 by a clotting enzyme contained in the hemocyte and activated by a bacterial endotoxin (lipopolysaccharide). Cleavage releases two chains of coagulin, A and B, linked by two disulfide bonds, together with the peptide C. Gel formation results from interlinking of coagulin molecules. Secondary structure prediction suggests the C peptide forms an alpha-helix, which is released during the proteolytic conversion of coagulogen to coagulin gel. The beta-sheet structure and 16 half-cystines found in the molecule appear to yield a compact protein stable to acid and heat.

While coagulogen is important for gel formation (e.g., clotting assay), the present disclosure has found that it is not essential in a chromogenic assay. The present disclosure has found that chromogenic assays comprising clarified LAL substantially free of coagulogen achieved increased levels of speed, sensitivity, and separation relative to chromogenic assays comprising LAL with naturally occurring amounts of coagulogen and which is not clarified. Thus, in some embodiments, the invention is directed to a chromogenic assay comprising clarified LAL substantially free of coagulogen.

In some embodiments, the clarified LAL is substantially free of coagulogen. For convenience, in some embodiments herein, LAL substantially free of coagulogen is also referred to as "LAL-co." One of skill in the art, upon reading the present disclosure, would appreciate that a reduction in various amounts of coagulogen will result in increasing levels of speed, sensitivity and/or separation in a chromogenic assay, e.g., an LAL assay. In some embodiments, the term "substantially free" refers to LAL having less than 50%, less than 40%, less than 30%, less than 20%, less than 10%, less than 5%, less than 2%, less than 1% or less than 0.5% (wt/wt) of coagulogen relative to total protein in the LAL as measured by SDS-PAGE with protein stain and confirmed by Western blot. In some embodiments, the term "substantially free" refers to LAL having less than 10% or less than 5% (wt/wt) of coagulogen relative to total protein in the LAL as measured by SDS-PAGE with protein stain and confirmed by Western blot. In some embodiments, the term "substantially free" refers to LAL having a concentration of coagulogen at less than about 20 μg/μL, less than about 15 μg/μL, less than about 10 μg/μL, less than about 5

µg/µL, less than about 4 µg/µL, less than about 3 µg/µL, less than about 2 µg/µL, or less than about 1 µg/µL. In some embodiments, the term "substantially free" refers to LAL having a concentration of coagulogen of 20 µg/µL to 0.001 µg/µL, 15 µg/µL to 0.01 µg/µL, 10 µg/µL to 0.1 µg/µL, 5 µg/µL to 0.5 µg/µL, 4 µg/µL to 0.5 µg/µL, 3 µg/µL to 0.5 µg/µL, 2 µg/µL to 0.5 µg/µL, or less than 1 µg/µL. In some embodiments, the term "substantially free" refers to LAL having a concentration of coagulogen of 10 µg/µL to 1 µg/µL, 5 µg/µL to 1 µg/µL, 4 µg/µL to 1 µg/µL, 3 µg/µL to 1 µg/µL, 2 µg/µL to 1 µg/µL, or less than 1 µg/µL. The concentration of coagulogen may be determined, e.g., using absorbance spectroscopy, quantification of an SDS-PAGE gel band or Western blot band, or any other method known to measure coagulogen concentration. In some embodiments, the measured concentration of coagulogen in the "LAL substantially free of coagulogen" cannot be precisely determined as it is within the margin of error of the minimum detection amount using conventional detection methods.

In some embodiments, the term substantially free LAL of coagulogen refers to LAL in which at least 60%, at least 70%, at least 80%, at least 90%, at least 95%, at least 97%, at least 98%, at least 99% or at least 99.5% (wt/wt) of coagulogen is removed relative to the amount of coagulogen in LAL in which the coagulogen has not been removed.

One of skill in the art can appreciate that different methods may be used to remove the coagulogen from the LAL. Each of these methods, may differ in efficiency, rate of purification, cost, and effort, but are within the knowledge of the skilled artisan. The present disclosure comprises a method of making clarified LAL substantially free of coagulogen using tangential flow filtration. Tangential flow filtration (TFF) refers to cross-flow filtration wherein the majority of the feed flow travels tangentially across the surface of the filter, rather than into the filter. By using TFF, the retentate comprising the majority of LAL proteins (which can foul the filter) is substantially washed away during the filtration process, and coagulogen is filtered into the permeate. In some embodiments, the TFF is a continuous process, i.e., continuous tangential flow filtration or continuous TFF, unlike batch-wise dead-end filtration. In some embodiments, continuous TFF comprises adding a diafiltration solution, i.e., water or buffer, to the sample at the same rate that permeate is generated, and thus the sample volume remains constant while the components that can freely permeate the filter are washed away. In some embodiments, diafiltration is a type of tangential flow filtration. Diafiltration refers to the fractionation process that washes smaller molecules through a membrane or filter and leaves larger molecules in the retentate without ultimately changing volume. A diafiltration volume, or DV, is the volume of sample before the diafiltration solution is added. In embodiments, using more diafiltration volumes in tangential flow filtration results in greater removal of permeate.

The term "clarified limulus amebocyte lysate" (or "clarified LAL") that is substantially free of coagulogen refers to LAL substantially free of coagulogen, discussed above, that has been further treated to remove components that create a cloudy appearance of the LAL. In embodiments, clarified LAL is created by centrifuging LAL substantially free of coagulogen. In some embodiments, the term "clarified LAL" refers to LAL that has been centrifuged at greater than 1800 g (i.e., 1800×gravity), greater than 2200 g, greater than 2600 g, greater than 3000 g, greater than 3400 g, greater than 3800 g, greater than 4200 g, greater than 4600 g, greater than 5000 g, greater than 5400 g, greater than 5800 g, greater than 6000 g, greater than 6100 g, or greater than 6200 g for a period of time sufficient visibly clear the LAL without damaging the enzymes. In some embodiments, the term "clarified LAL" refers to LAL that has been centrifuged at 1800 to 8000 g, 2200 g to 7600 g, 2600 g to 7200 g, 3000 g to 7200 g, 3400 g to 7200 g, 3800 g to 7200 g, 4200 g to 7200 g, 4600 g to 7200 g, 5000 g to 7200 g, 5400 g to 7200 g, 5800 g to 7200 g, or 6100 g to 7200 g for a period of time sufficient visibly clear the LAL without damaging the enzymes.

In some embodiments, the term "clarified limulus amebocyte lysate" (or "clarified LAL") that is substantially free of coagulogen refers to LAL substantially free of coagulogen, discussed above, that has been further treated to remove components that create a cloudy appearance of the LAL by the centrifuging LAL substantially free of coagulogen at greater than 20,000×g, greater than 22,000×g, greater than 24,000×g, greater than 25,000×g, greater than 26,000×g, greater than 28,000×g, greater than 30,000×g, greater than 35,000×g, greater than 40,000×g, greater than 45,000×g or greater than 50,000×g. In some embodiments, the LAL substantially free of coagulogen is centrifuged a at greater than 20,000-50,000×g, 20,000-40,000×g, 25,000-50,000×g, 25,000-40,000×g, or 30,000-40,000×g. In some embodiments, the LAL substantially free of coagulogen is centrifuged for greater than 20 minutes, greater than 30 minutes, greater than 40 minutes or greater than 60 minutes. In some embodiments, the LAL substantially free of coagulogen is centrifuged for 20-120 minutes, 20-90 minutes, 20-60 minutes, 20-40 minutes or about 30 minutes.

In some embodiments, the term "clarified LAL" refers to LAL that has been centrifuged for greater than 3 minutes, greater than 4 minutes, greater than 5 minutes, greater than 6 minutes, greater than 7 minutes, greater than 8 minutes, greater than 9 minutes, or greater than 10 minutes. In some embodiments, the term "clarified LAL" refers to LAL that has been centrifuged for 3 minute to 30 minutes, 4 minutes to 25 minutes, 4 minutes to 20 minutes, 5 minutes to 15 minutes or 5 minutes to 10 minutes. One of skill in the art can appreciate that a lower speed of centrifugation may require a longer centrifugation time, and will adjust the time and/or speed accordingly to reduce the visual cloudiness of the LAL. In some embodiments, the term "clarified LAL" refers to LAL substantially free of coagulogen centrifuged at about 5000 g to about 7000 g for about 3 minutes to about 10 minutes, or about 6120 g for 5 minutes. In embodiments, clarified LAL substantially free of coagulogen is made by centrifuging a solution derived from lysed amebocytes from *Limulus polyphemus* at 2,000 rpm (980 g) for 8 minutes at 4° C. The clarified LAL is found in the supernatant after centrifugation. In some embodiments the resulting supernatant is then combined with a buffer; the resulting combination of supernatant and buffer is then subjected to tangential flow filtration using a 30 kDa membrane filter to produce a retentate; and the retentate is centrifuged at 5,000 rpm (6120 g) for 5 minutes at 4° C. to produce a supernatant, wherein the supernatant is clarified LAL that is substantially free of coagulogen. In embodiments, the solution derived from lysed amebocytes from *Limulus polyphemus* is a pool of multiple *Limulus polyphemus* lysed amebocytes.

In some embodiments, clarified LAL substantially free of coagulogen is made by obtaining a solution derived from lysed amebocytes from *Limulus polyphemus*. In some embodiments, the solution is then combined with a buffer; the resulting combination of solution and buffer is then subjected to continuous tangential flow filtration (TFF) using a 20 kDa to 50 kDa membrane filter to produce a retentate; and the retentate is centrifuged at greater than 20,000×g for greater than 25 minutes at 4° C. to produce a supernatant, wherein the supernatant is clarified LAL that is substantially free of coagulogen. In embodiments, the solution derived from lysed amebocytes from *Limulus polyphemus* is a pool of multiple *Limulus polyphemus* lysed amebocytes. In some embodiments, the continuous TFF comprises at least four diafiltration volumes (DV). In some embodiments, the continuous TFF comprises at least five diafiltration volumes. In some embodiments, the continuous TFF comprises at least six diafiltration volumes. In some embodiments, the continuous TFF comprises at least 7, at least 8, at least 9, at least 10, at least 11, at least 12, at least 13, at least 14, or at least 15 diafiltration volumes.

In some embodiments, clarified LAL substantially free of coagulogen according to the present disclosure is produced by a method utilizing any combination of the technical features described herein. Thus, one of skill in the art can use any of the listed filters, filter sizes, filter flow rates, buffers, centrifugation speeds, centrifugation temperatures, centrifugation times, etc., sufficient to make the LAL substantially free of coagulogen. For example, in some embodiments, the LAL (i) is centrifuged at greater than 20,000×g, greater than 22,000×g, greater than 24,000×g, greater than 25,000×g, greater than 26,000×g, greater than 28,000×g, greater than 30,000×g, greater than 35,000×g, greater than 40,000×g, greater than 45,000×g or greater than 50,000×g, (ii) is centrifuged at a temperature of 2° C. to 10° C., 2° C. to 8° C., or 4° C., (iii) is centrifuged for 20-120 minutes, 20-90 minutes, 20-60 minutes, 20-40 minutes or about 30 minutes, (iv) undergoes TFF at a flow rate of greater than 500 mL/min, e.g., 500 mL/min to 2000 mL/min, 800 mL/min to 1500 mL/min, or 1000 mL/min to 1200 mL/min, (v) undergoes TFF using a 50 kDa filter, a 45 kDa filter, a 40 kDa filter, a 35 kDa filter, a 30 kDa filter, a 25 kDa filter, or a 20 kDa filter, (vii) undergoes TFF using at least 4 DV, at least 5 DV, at least 6 DV, at least 7 DV, or at least 8 DV, etc.

In some embodiments, the chromogenic assay determines the presence or absence of endotoxin in a sample. In other embodiments, the chromogenic assay can quantify the amount of endotoxin in a sample. In some embodiments, the method further comprises comparing the chromogenic effect of the endotoxin in a sample to a known endotoxin standard to determine the quantity of endotoxin in the sample.

In some embodiments, the disclosure is directed to a method of detecting an endotoxin in a biological sample using a chromogenic assay, the method comprising: (a) contacting the biological sample with an aqueous reagent comprising clarified limulus amebocyte lysate (LAL) and Ac-Ile-Glu-Ala-Arg-pNA; (b) measuring the change in absorbance at 405 nm resulting from the enzymatic cleavage of pNA from Ac-Ile-Glu-Ala-Arg-pNA in the presence of endotoxin in the sample, wherein the LAL is substantially free of coagulogen.

In embodiments, the invention provides a method of detecting an endotoxin in a sample using a chromogenic assay, the method comprising (a) combining a first solution comprising 30% to 60% (v/v) clarified LAL substantially free of coagulogen with a second solution comprising a chromogenic substrate to produce a third solution, wherein 75%-85% (v/v) of the third solution is the first solution, and 15%-25% (v/v) of the third solution is the second solution; (b) combining the third solution with a sample containing endotoxin; and (c) measuring a change in absorbance of the chromogenic substrate. In embodiments, the invention provides a method of detecting an endotoxin in a sample using a chromogenic assay, the method comprising (a) combining a first solution comprising 50% (v/v) clarified LAL substantially free of coagulogen with a second solution comprising a chromogenic substrate to produce a third solution, wherein 80% (v/v) of the third solution is the first solution, and 20% (v/v) of the third solution is the second solution; (b) combining the third solution with a sample containing endotoxin; and (c) measuring a change in absorbance of the chromogenic substrate. In embodiments, the first solution also comprises buffer and detergent. In embodiments, the invention provides a method of detecting an endotoxin in a sample using a chromogenic assay, the method comprising (a) contacting a solution comprising 35 to 45% (v/v) clarified LAL substantially free of coagulogen and 15% to 25% (v/v) chromogenic substrate with a biological sample, and (b) measuring a change in absorbance of the chromogenic substrate. In embodiments, the invention provides a method of detecting an endotoxin in a sample using a chromogenic assay, the method comprising (a) contacting a solution comprising 40% (v/v) clarified LAL substantially free of coagulogen and 20% (v/v) chromogenic substrate with a biological sample, and (b) measuring a change in absorbance of the chromogenic substrate. In embodiments, the solution comprising clarified LAL substantially free of coagulogen further comprises buffer and detergent.

In embodiments, by removing the coagulogen from the LAL and clarifying the coagulogen-free LAL, the chromogenic assay surprisingly has increased sensitivity. In some embodiments, the method has a sensitivity of 0.0001 EU/mL to 1.0 EU/mL endotoxin. In embodiments, the method has a sensitivity of 0.0005 EU/mL to 1.0 EU/mL endotoxin, 0.008 EU/mL to 1.0 EU/mL endotoxin, 0.001 EU/mL to 1.0 EU/mL endotoxin, 0.005 EU/mL to 1.0 EU/mL endotoxin, 0.01 EU/mL to 1.0 EU/mL endotoxin, 0.02 EU/mL to 1.0 EU/mL endotoxin, 0.03 EU/mL to 1.0 EU/mL endotoxin, or 0.05 EU/mL to 1.0 EU/mL endotoxin. In embodiments, less than 0.05 EU/mL, less than 0.03 EU/mL, less than 0.01 EU/mL, less than 0.008 EU/mL, less than 0.006 EU/mL, less than 0.005 EU/mL, less than 0.004 EU/mL, less than 0.003 EU/mL, less than 0.002 EU/mL, or less than 0.001 EU/mL.

In some embodiments, clarified LAL-co results in a reaction profile which is smoother relative to LAL-co that has not been clarified. In some embodiments, the reaction profile between separate batches is more consistent because the reaction profile is smoother. In some embodiments, the reaction profile of clarified LAL-co fits to a curve better relative to LAL-co that has not been clarified.

In some embodiments, clarified LAL-co results in a reaction profile which is smoother relative to LAL-co that has not been clarified. In some embodiments, the reaction profile between separate batches is more consistent because the reaction profile is smoother. In some embodiments, the reaction profile of clarified LAL-co fits to a curve better relative to LAL-co that has not been clarified.

In some embodiments, the clarified LAL-co more quickly reaches a designated optical density relative to LAL-co that has not been clarified. In some embodiments, the clarified LAL-co more quickly reaches 30 mOD relative to LAL-co that has not been clarified. In some embodiments, the clarified LAL-co reaches 30 mOD 20%, 30%, 40%, 50%, 60%, 70%, or 80% more quickly relative to LAL-co that has not been clarified. In some embodiments, the clarified LAL-co more quickly reaches 50 mOD relative to LAL-co that has not been clarified. In some embodiments, the clarified LAL-co reaches 50 mOD 20%, 30%, 40%, 50%, 60%, 70%, or 80% more quickly relative to LAL-co that has not been clarified.

In some embodiments, the clarified LAL-co has a larger separation (in time) between a 0 EU/mL standard (blank standard) and a 0.005 EU/mL standard relative to LAL-co that has not been clarified. In some embodiments, the clarified LAL-co has a separation 20%, 30%, 40%, 50%, 60%, 70%, or 80% larger (in time) between a 0 EU/mL standard (blank standard) and a 0.005 EU/mL standard relative to LAL-co that has not been clarified. In some embodiments, the clarified LAL-co has a larger separation (in time) between a 0 EU/mL standard (blank standard) and a 0.0005 EU/mL standard relative to LAL-co that has not been clarified. In some embodiments, the clarified LAL-co has a separation 20%, 30%, 40%, 50%, 60%, 70%, or 80% larger (in time) between a 0 EU/mL standard (blank standard) and a 0.0005 EU/mL standard relative to LAL-co that has not been clarified. The invention further provides a composition comprising (a) clarified LAL substantially free of coagulogen ("LAL-co") and (b) buffer. In embodiments, such a composition comprises 30% to 60% (v/v) clarified LAL-co, and in embodiments 40% to 60% (v/v), and in embodiments, 50% (v/v) clarified LAL-co. In embodiments, the invention provides a composition comprising (a) clarified LAL substantially free of coagulogen, (b) buffer and (c) a detergent. In embodiments, such a composition comprises 30% to 60% clarified LAL substantially free of coagulogen, and in embodiments 40% to 60% (v/v), and in embodiments, 50% clarified LAL-co. In embodiments, the compositions of the invention comprising clarified LAL substantially free of coagulogen comprises Tris buffer at a pH of 7.4-7.5. In embodiments, the compositions of the invention comprising clarified LAL substantially free of coagulogen comprise Tris buffer, sodium chloride, trehalose and magnesium chloride. In embodiments, the compositions of the invention comprises clarified LAL substantially free of coagulogen, about 25 mM to about 50 mM Tris buffer, about 80 mM sodium chloride, about 70 mM trehalose and about 10 mM magnesium chloride. In embodiments, the compositions of the invention comprises clarified LAL substantially free of coagulogen, about 50% LAL-co, about 50 mM Tris buffer, about 75 mM trehalose, about 77 mM sodium chloride, and about 10 mM magnesium chloride and is at a pH of 7.4-7.5. In embodiments, the invention provides a composition comprising clarified LAL substantially free of coagulogen, buffer, and a zwitterionic detergent that retains its zwitterionic character over a wide pH range. In embodiments, the buffer is n-Tetradecyl-N,N-dimethyl-3-ammonio-1-propane-sulfonate (ZWITTERGENT® 3-14 detergent) having molecular formula C19H41NO3S. In embodiments, the detergent is present at about 0.2 mM to 0.5 mM, about 0.3 mM to 0.4 mM or about 0.44 mM in the composition comprising clarified LAL substantially free of coagulogen. In embodiments, the compositions of the invention comprise clarified LAL substantially free of coagulogen, about 25 mM to about 50 mM Tris buffer, about 20 mM to about 90 mM trehalose, about 80 mM sodium chloride, and about 10 mM magnesium chloride. In embodiments, the compositions of the invention comprises about 50% LAL-co, about 50 mM Tris buffer, about 75 mM trehalose, about 77 mM sodium chloride, about 10 mM magnesium chloride, and about 0.44 mM n-Tetradecyl-N,N-dimethyl-3-ammonio-1-propane-sulfonate (ZWITTERGENT® 3-14 detergent) having molecular formula C19H41NO3 S, and is at a pH of about 7.4-7.5.

The disclosure is further directed to compositions comprising clarified LAL, wherein the composition is substantially free of coagulogen, wherein the composition is made by a method comprising: centrifuging a solution derived from lysed amebocytes from *Limulus polyphemus* at 2,000 rpm for 8 minutes at 4° C. to produce a supernatant; combining the supernatant from (a) with a buffer; subjecting the combination from (b) to tangential flow filtration using a 30 kDa membrane filter to produce a retentate; and centrifuging the retentate from (c) at 5000 rpm (e.g., 6120 g) for 5 minutes at 4° C. to produce a supernatant, wherein the supernatant is clarified LAL that is substantially free of coagulogen.

The disclosure additionally is directed to compositions comprising (1) clarified LAL substantially free of coagulogen, buffer and detergent, and (2) a chromogenic substrate. In some embodiments, the chromogenic substrate in the composition comprises pNA. In some embodiments, the chromogenic substrate in the composition is Ac-lle-Glu-Ala-Arg-pNA. In some embodiments, the composition comprises 30% to 50% clarified LAL substantially free of coagulogen preparation, and 10% to 30% chromogenic substrate (v/v). In some embodiments, the composition comprises about 35% to about 45% clarified LAL substantially free of coagulogen and 15% to 25% chromogenic substrate. In some embodiments, the composition comprises 40% LAL substantially free of coagulogen preparation, and 20% chromogenic substrate (wt/wt). In some embodiments, the composition comprises about 40% clarified LAL substantially free of coagulogen preparation, and 20% Ac-lle-Glu-Ala-Arg-pNA (wt/wt). In some embodiments, the compositions as described herein are in a single container, e.g., a single vial. In some embodiments, the compositions described herein are lyophilized. For example, the disclosure specifically describes a lyophilized composition comprising 40% LAL substantially free of coagulogen preparation, and 30% Ac-lle-Glu-Ala-Arg-pNA (wt/wt).

In some embodiments, the present invention is directed to a chromogenic assay kit. The kit can include one or more of the components normally associated with a LAL chromogenic assay, including a reagent comprising clarified LAL and a chromogenic substrate. In some embodiments, the method of the present disclosure is directed to a kit comprising: (a) clarified limulus amebocyte lysate (LAL), wherein the LAL is substantially free of coagulogen; (b) a chromogenic substrate; and (c) instructions for detecting an endotoxin using the LAL and chromogenic substrate. In some embodiments, the kit comprises various reagents, each reagent containing clarified LAL with a different amount of coagulogen removed.

The kit can comprise one or more containers. In some embodiments, the clarified LAL and the chromogenic substrate are in a single container. In some embodiments, the clarified LAL and the chromogenic substrate are in two distinct containers. In some embodiments, the kit comprises a sterile container comprising the clarified LAL. In some embodiments, the kit comprises a reconstitution buffer, which can reconstitute the clarified LAL and/or the chromogenic substrate for use in the assay. In some embodiments, the sterile container is a sterile vial. In some embodiments, the kit further comprises a control standard endotoxin, which can be used as a positive endotoxin control, or can be used to quantitate the amount of endotoxin in a standard. In some embodiments, the kit comprises more than one control standard endotoxin, at one or more concentrations.

One of skill in the art can appreciate that different methods may be used to remove the coagulogen from the LAL. Each of these methods, may differ in efficiency, rate of purification, cost, and effort, but are within the knowledge of the skilled artisan. The present disclosure comprises a method of making clarified LAL substantially free to coagulogen using tangential flow filtration. Tangential flow filtration (TFF) refers to cross-flow filtration wherein the majority of the feed flow travels tangentially across the surface of the filter, rather than into the filter. By using TFF, the retentate comprising the majority of LAL proteins (which can foul the filter) is substantially washed away during the filtration process, and coagulogen is filtered into the permeate. In some embodiments, the TFF is a continuous process, unlike batch-wise dead-end filtration.

In some embodiments, the disclosure is directed to a method of making clarified LAL substantially free of coagulogen, the method comprising centrifuging a solution derived from lysed amebocytes from *Limulus polyphemus* at 1000 to 3000 rpm for 2 to 15 minutes at 2 to 10° C. to produce a first supernatant ("the first centrifuging"); combining the supernatant with a buffer; filtering the combination using a 20 kDa to 50 kDa filter to produce a retentate; centrifuging the retentate at 3000 to 7000 rpm for 2 to 10 minutes at 2 to 10° C. to produce a second supernatant ("the second centrifuging"), wherein the second supernatant comprises clarified LAL that is substantially free of coagulogen. In embodiments, the filtering is subjecting the LAL to TFF. In some embodiments, then LAL is placed in a buffer prior to TFF. In some embodiments, the buffer is a Tris buffer or MES buffer. In some embodiments, the buffer has a pH of about 6.0 to about 9.0, or about 7.0 to about 8.0. In embodiments, the first centrifuging comprises centrifuging at 2000 rpm. In embodiments, the first centrifuging comprises centrifuging for 8 minutes. In embodiments, the first centrifuging comprises centrifuging at 4° C. In embodiments, the second centrifuging comprises centrifuging at 5000 rpm. In embodiments, the second centrifuging comprises centrifuging for 5 minutes. In embodiments, the second centrifuging comprises centrifuging at 4° C.

Various membranes can be used in the TFF. Filters of varying pore sizes can be used in TFF, depending on the size of the desired protein to be reduced in the resulting retentate. In the present disclosure, Factor C, Factor B, Factor G and proclotting enzyme are known to be involved in the clotting cascade system of LAL, resulting in the conversion of coagulogen into an insoluble coagulin gel. For purposes of the disclosure provided herein, any TFF procedure (and accompanying filter pore size, pore type and buffer system) can be used which results in coagulogen being reduced, and Factor C, Factor B, Factor G and proclotting enzyme being retained. Thus, in some embodiments, the TFF procedure uses a 50 kDa filter, a 45 kDa filter, a 40 kDa filter, a 35 kDa filter, a 30 kDa filter, a 25 kDa filter, or a 20 kDa filter. In some embodiments, a 40 kDa to a 25 kDa filter is used. In some embodiments, the membrane is a 10 to 80 kDa filter, or a 20 to 50 kDa filter. In some embodiments, the filter is a 30 kDa filter.

The membranes use in the method disclosed herein can include, but are not limited to modified Polyethersulfone (mPES), Polysulfone (PS) and Polyethersulphone (PES). In some embodiments, the method of making LAL substantially free of coagulogen is performed using TFF using a modified polyethersulfone (mPES) membrane filter. The rate of flow of the LAL across the membranes can be adjusted to optimize removal of the coagulogen from the LAL. In some embodiments, the TFF is performed at a flow rate of 200 mL/min to 800 mL/min, 300 mL/min to 600 mL/min, or 350 mL/min to 500 mL/min. In some embodiments, the TFF is performed at a flow rate of greater than 500 mL/min, e.g., 500 mL/min to 2000 mL/min, 800 mL/min to 1500 mL/min, or 1000 mL/min to 1200 mL/min. In some embodiments, the TFF is performed at 1000 mL/min, 1100 mL/min, 1200 mL/min, 1300 mL/min or 1400 mL/min. In some embodiments, the TFF is performed at 1100 mL/min.

In embodiments, the invention provides a method of producing clarified LAL substantially free of coagulogen through centrifuging LAL that is substantially free of coagulogen.

EXAMPLES

Example 1

Improved Detection of Endotoxin with Clarified LAL-Co

The reaction speed and sensitivity of a chromogenic endotoxin assay of samples containing LAL substantially free of coagulogen (LAL-co) and clarified LAL-co were tested on a 96-well plate, as shown in FIG. 1. Rows A-F include increasing amounts of endotoxin standard. A first solution containing 50% LAL-co or clarified LAL-co was combined with a second solution containing chromogenic substrate to form a third and final solution, which was then contacted with a sample containing endotoxin. In columns 1-3 of FIG. 1, the third solution contained 50% clarified LAL-co first solution, and 50% second solution (i.e., 25% of the final third solution contained clarified LAL-co) (50/50/50 solution). In columns 4-6 of FIG. 1, the third solution contained 80% clarified LAL-co solution, and 20% second solution (i.e., 40% of the final third solution contains clarified LAL-co) (50/80/20 solution). In columns 7-9 of FIG. 1, the third solution contained 50% whole LAL-co solution, and 50% second solution (i.e., 25% of the final solution contains whole LAL-co). In columns 10-12 of FIG. 1, the third solution contains 80% whole LAL-co solution, and 20% second solution (i.e., 40% of the final solution contains whole LAL-co).

Figure 4:
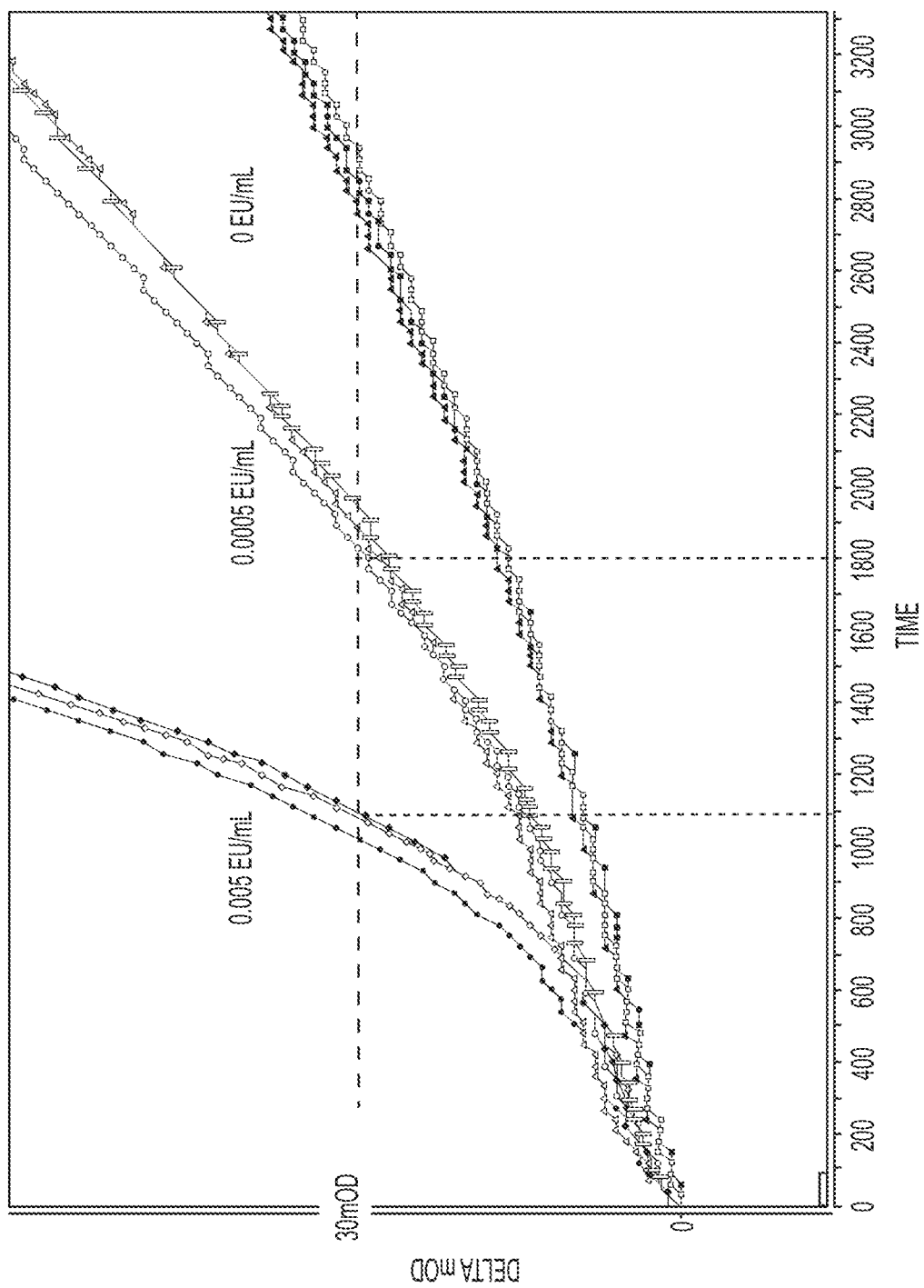
FIG. 4: An embodiment of the method of detecting endotoxin using a chromogenic assay, showing improved assay performance, e.g., a smooth reaction profile and a large separation from the 0 EU/mL control.

FIG. 1 illustrates that using clarified LAL-co and a formulation with more LAL-co and less substrate surprisingly provides speed and increased separation between the blank separation with smooth reaction profiles. FIG. 4 further illustrates this observation. Three different 50/80/20 solutions were prepared and tested with standards of 0.0005 EU/mL and 0.005 EU/mL. These clarified LAL-co solutions had an average 30 mOD time of 31 minutes and 17 minutes, respectively. The reaction curves were smoother, and more consistent. Additionally, there was a larger separation in time between the 0 EU/mL sample and 0.0005 EU/mL sample (940 seconds) and the 0 EU/mL sample and 0.005 EU/mL sample (1755 seconds). Thus, the clarified LAL-co results in improved assay performance (e.g., increased speed of reaction, greater differentiation from 0 EU/mL control), lower amounts of substrate, and the smoother reaction curve results in more consistency.

Example 2

Preparing Clarified LAL-co

Figure 2:
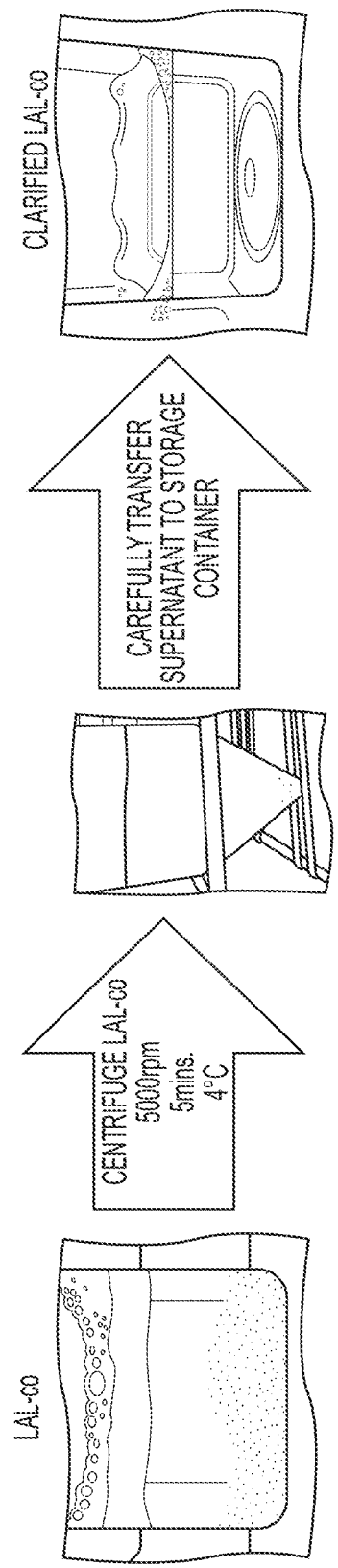
FIG. 2: Visual comparison of LAL substantially free of coagulogen ("LAL-co") versus an embodiment of clarified LAL-co that was prepared by centrifuging LAL-co at 5000 rpm for 5 minutes at 4° C.
Figure 3:
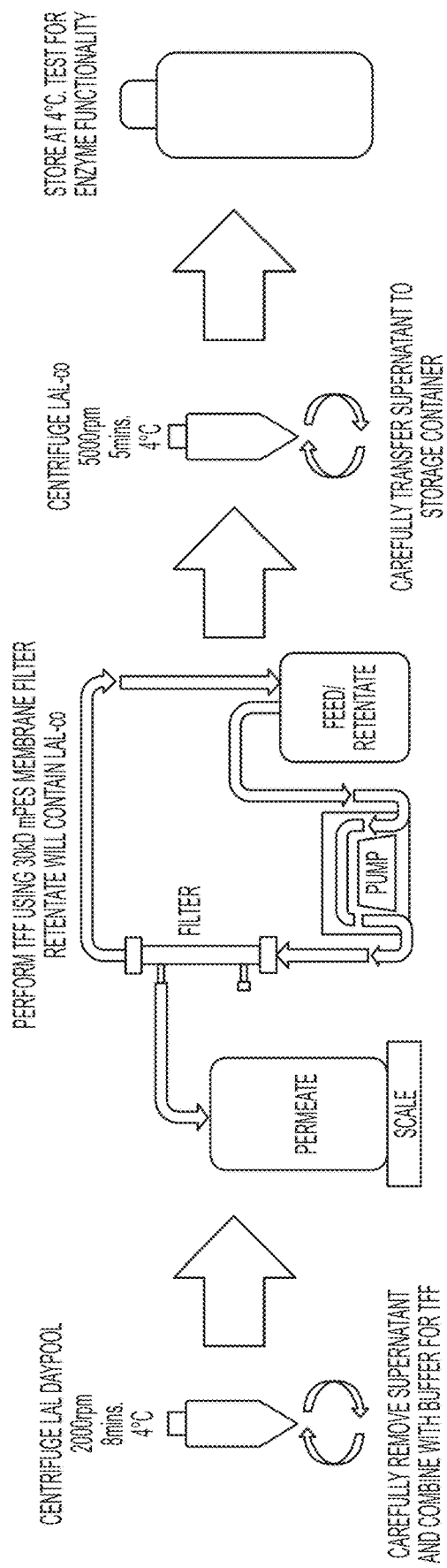
FIG. 3: Schematic of an embodiment of a method of preparing clarified LAL that is substantially free of coagulogen. Multiple *Limulus polyphemus* lysed amebocyte batches are pooled together ("LAL Daypool") and centrifuged, the resulting supernatant is filtered using tangential flow filtration to produce a retentate that contains LAL substantially free of coagulogen, followed by centrifugation of the retentate to produce a supernatant that clarified LAL substantially free of coagulogen.

FIG. 3 is a schematic illustrating a method of preparing clarified LAL-co. First, multiple batches of lysed amebocyte from *Limulus polyphemus* were pooled to form LAL Daypool. The LAL Daypool was centrifuged at 2000 rpm for 8 minutes at 4° C. The supernatant was carefully removed and combined with buffer. The resulting solution was filtered by tangential flow filtration (TFF) using a 30 kDa mPES membrane filter. The retentate contained LAL-co. The retentate was then centrifuged at 5000 rpm for 5 minutes at 4° C. (see FIG. 2), and the supernatant was transferred to a storage container and stored at 4° C.

Example 3

Stability of LAL Daypools Used to Form Clarified LAL Substantially Free of Coagulogen The stability of LAL Daypools used to form clarified LAL-co was investigated using standards of 0.0005 EU/mL and 0.005 EU/mL. LAL Daypools were stored for 1 year, 2 years and 3 years and used to form clarified LAL-co. At the end of the indicated time period, the clarified LAL-co sample was used to form a solution containing 50% clarified LAL-co, which was then mixed with the LAL chromogenic reagent, at an 80:20 ratio, and was placed in a 96-well plate and then placed in an incubating plate reader that measured absorbance at 405 nm. The reaction was automatically monitored over time the appearance of a yellow color.

Figure 5:
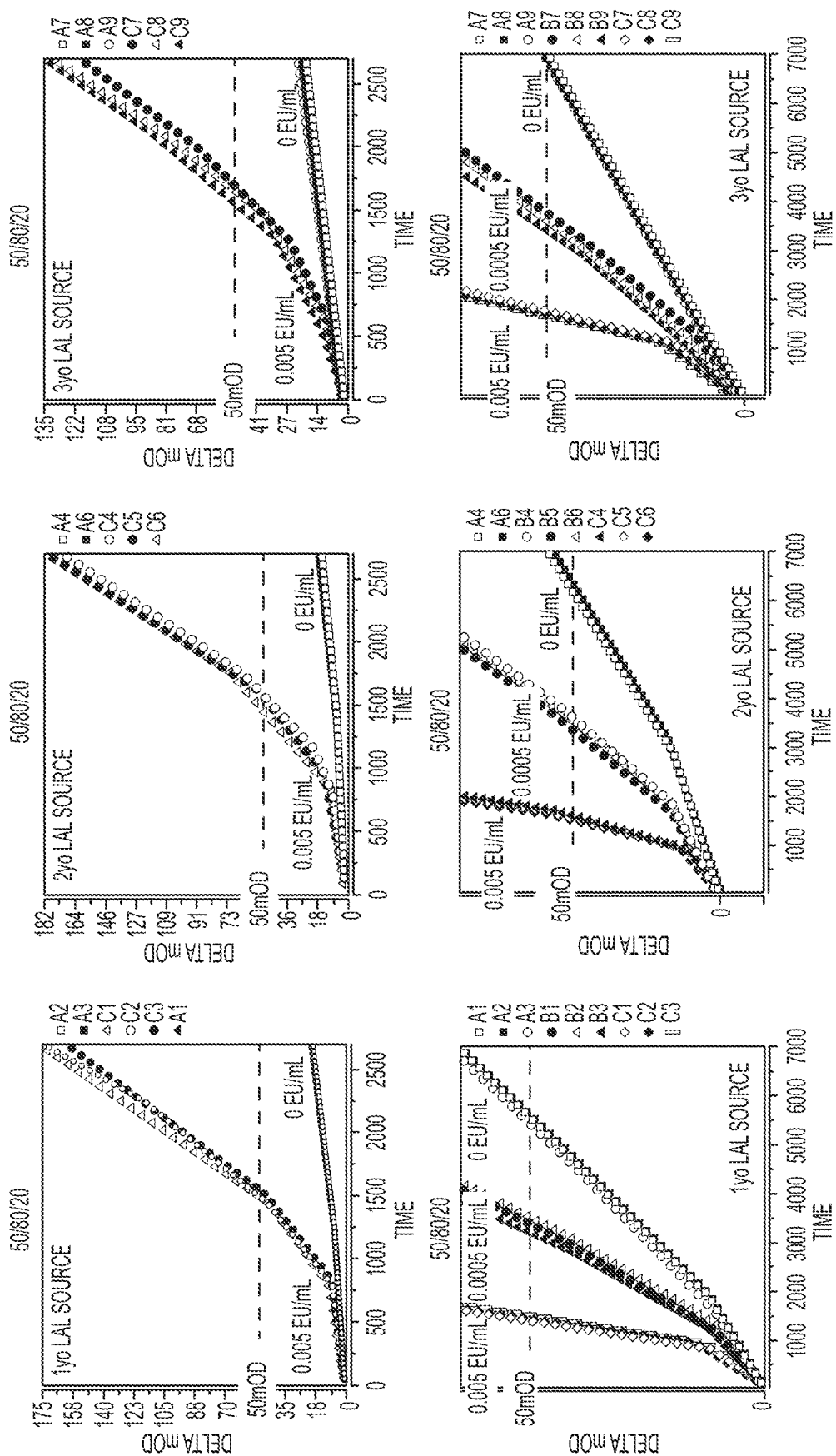
FIG. 5: Change in optical density as a function of time for clarified LAL substantially free of coagulogen for 1 year old, 2 year old and 3 year old LAL sources in formulations containing 40% (v/v) clarified coagulogen-free LAL and 20% chromogenic substrate (50/80/20 formulation).
Figure 7:
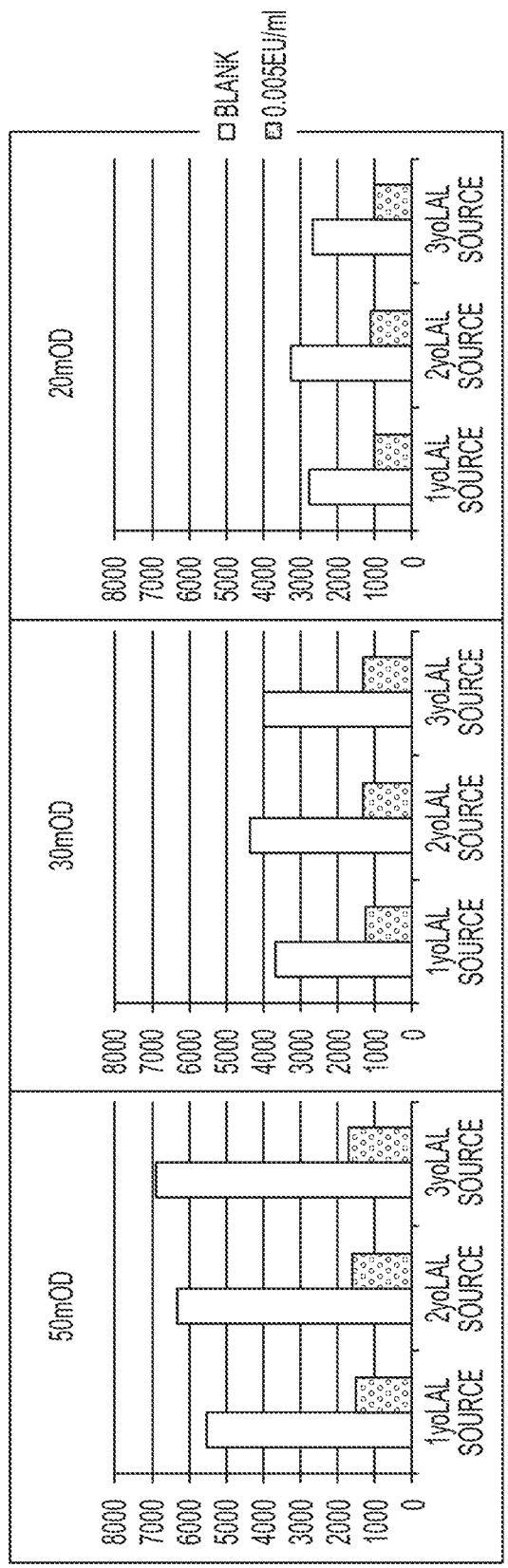
FIG. 7: Bar graph showing time (seconds) for the 50/80/20 formulation to reach 50 mOD, 30 mOD and 20 mOD in a chromogenic assay of the invention as a function of age of the source of clarified LAL-co (1 year, 2 year or 3 year) with either 0.005 EU/mL standard (right column) or blank standard (left column).
Figure 8:
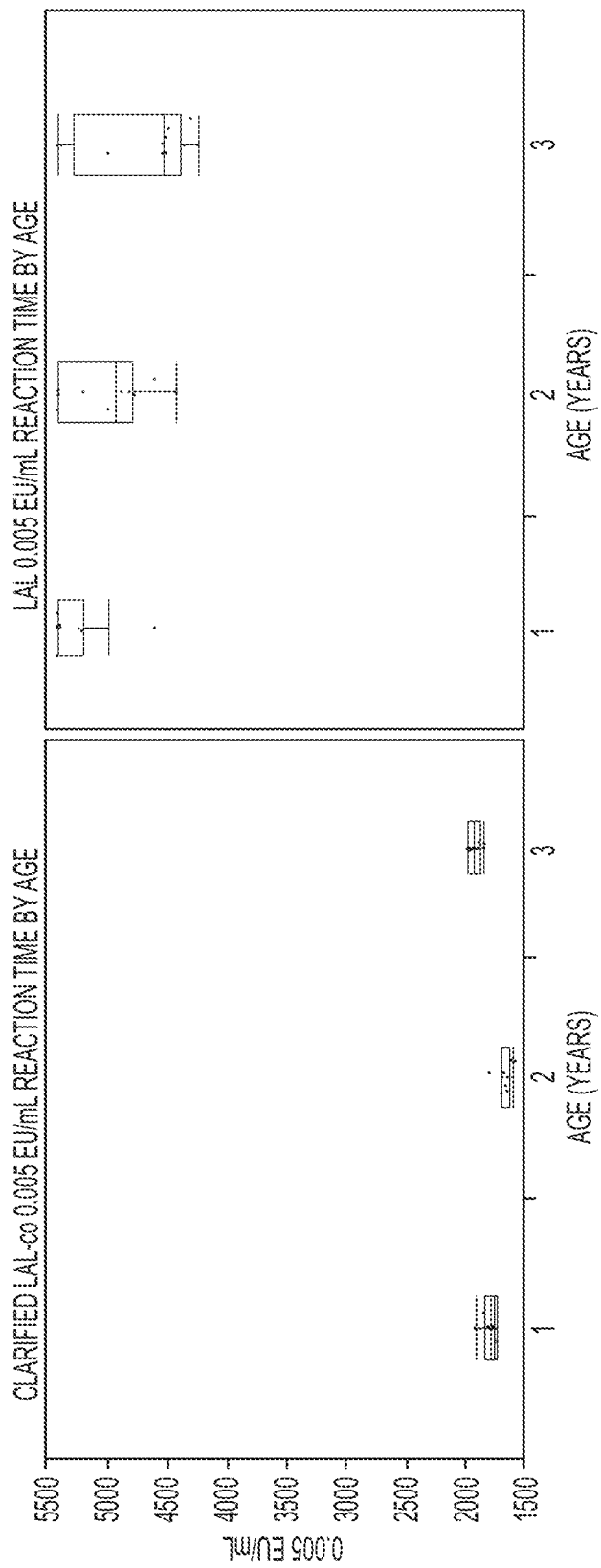
FIG. 8: Box plot of reaction time for 0.005 EU/mL standard for clarified LAL substantially free of coagulogen for 1 year old, 2 year old and 3 year old LAL sources in formulations containing 40% (v/v) clarified coagulogen-free LAL and 20% chromogenic substrate (50/80/20 formulation). Box plot of reaction time for 0.005 EU/mL standard for LAL for 1 year old, 2 year old and 3 year old LAL sources in formulations containing 40% (v/v) LAL and 20% chromogenic substrate (50/80/20 formulation).
Figure 9:
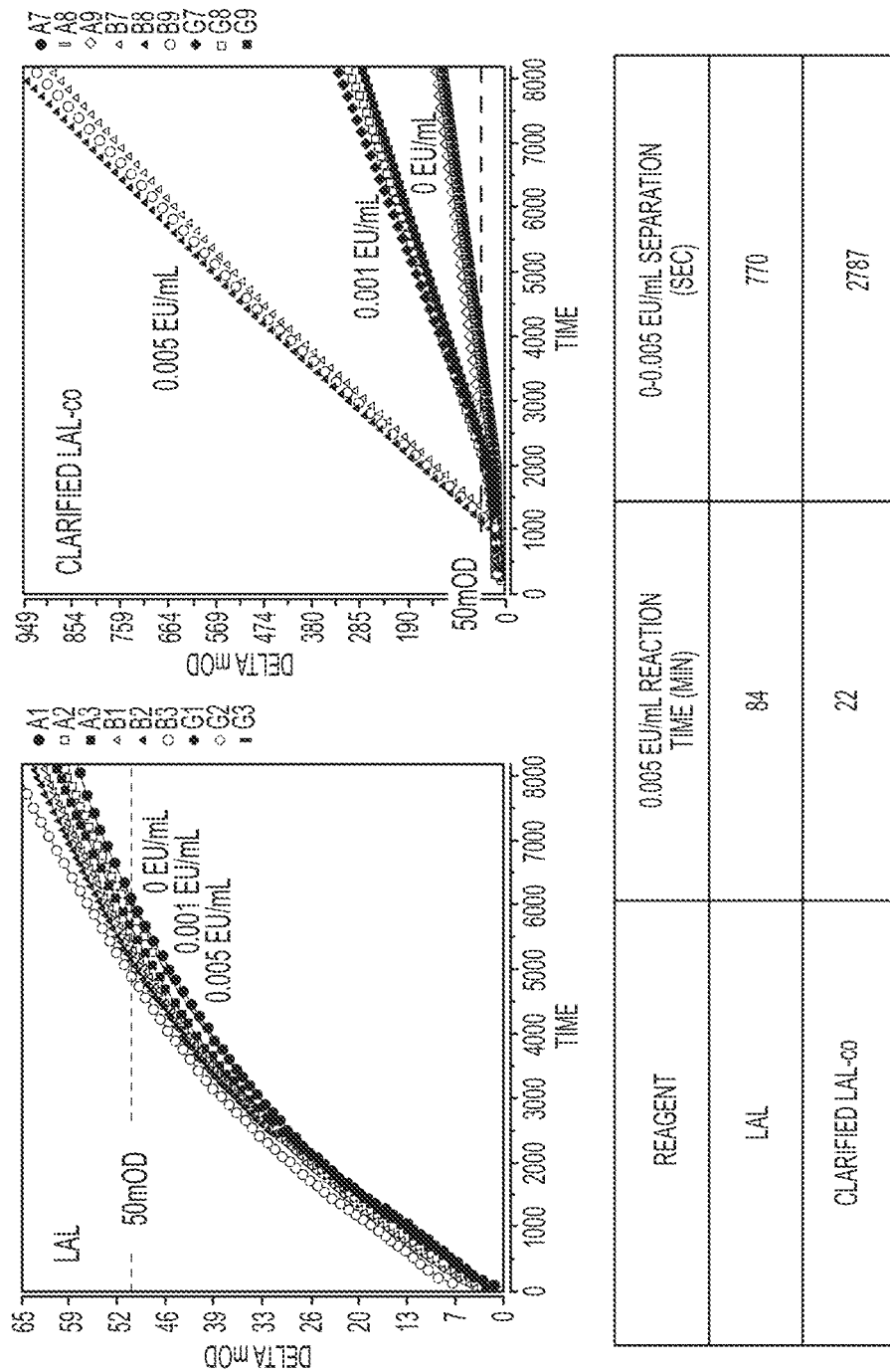
FIG. 9: Change in optical density as a function of time for clarified LAL substantially free of coagulogen in formulations containing 40% (v/v) clarified coagulogen-free LAL and 20% chromogenic substrate (50/80/20 formulation). Change in optical density as a function of time for LAL in formulations containing 40% (v/v) LAL and 20% chromogenic substrate (50/80/20 formulation). Table compares reaction times for the 0.005 EU/mL standard and separation between reactions times for the 0.005 EU/mL and 0 EU/mL blank.

In the presence of endotoxin, the lysate will cleave the chromogenic substrate, causing the solution to become yellow. The time required for the change is inversely proportional to the amount of endotoxin present. The reaction and separation time for each of the samples is found in FIG. 5, FIG. 6, FIG. 7, FIG. 8, AND FIG. 9. FIGS. 5, 6 and 7 are from the same samples and experiments. FIGS. 8 and 9 are from the same examples and experiments. The x-axis of FIG. 5 is time (seconds), the y axis is change in mOD. The y-axis of FIG. 7 is time (seconds). The data suggests that LAL Daypools used to form clarified LAL-co are stable for at least 3 years, and maintain their increased reaction time, smooth reaction curve, and larger separation between the blank standard (0 EU/mL) and endotoxin controls (0.005 EU/mL and 0.0005 EU/mL). The y-axis of FIG. 8 is 0.005 EU/mL reaction time in seconds, the x-axis represents LAL sources of different ages. The plot on the left is data from clarified LAL-co and the right is from untreated LAL. The data suggests that differences in performance of LAL over time can be overcome by treating the LAL using TFF and centrifugation of the resulting LAL-co. The y-axis of graphs in FIG. 9 shows the change in mOD, the x axis is time in seconds. The table contains reaction times retrieved from the graph for the 0.005 EU/mL standard and the separation between this time and the 0 EU/mL blank. The data suggests that clarified LAL-co has a faster reaction time for standards, and greater separation between blank and low standards, than its untreated LAL counterpart.

Example 4

Figure 10:
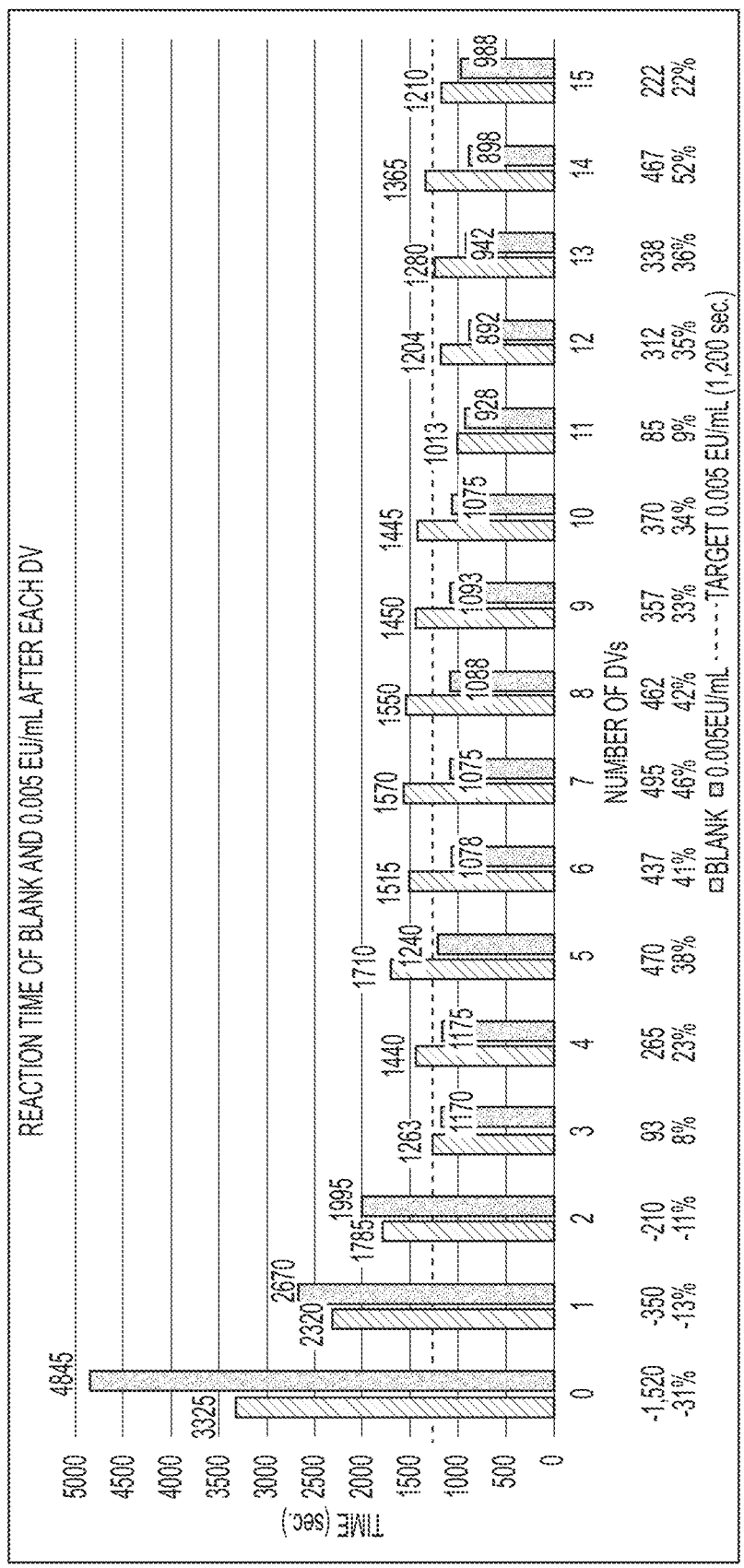
FIG. 10: Comparison of reaction time with 0 EU/mL blank or 0.005 EU/mL retentate after each diafiltration volume (DV) of continuous tangential flow filtration using a 30 kDa filter. The target reaction time for the 0.005 EU/mL retentate is 1200 seconds, indicated by the dotted line. Numbers below each set of bars represents the absolute ("Sepa. (sec.)") and percentage ("% Sepa.") difference between the reaction time of the blank and reaction time of the 0.005 EU/mL. A positive difference indicates that the blank reacted slower than the 0.005 EU/mL. A negative difference indicates that the blank reacted faster than the 0.005 EU/mL.

Various diafiltration volumes (DV) of continuous tangential flow filtration were investigated to determine which volume produced the best sensitivity (comparing a blank to a 0.005 EU/mL standard) while achieving a reaction time of 1200 seconds. See, FIG. 10. It was found that greater than 4 DV removed coagulogen to achieve a reaction time of less than 1200 seconds. Five, six and seven DV produced the desired reaction time, while producing the highest sensitivity and minimizing the diafiltration volumes.

Figure 11:
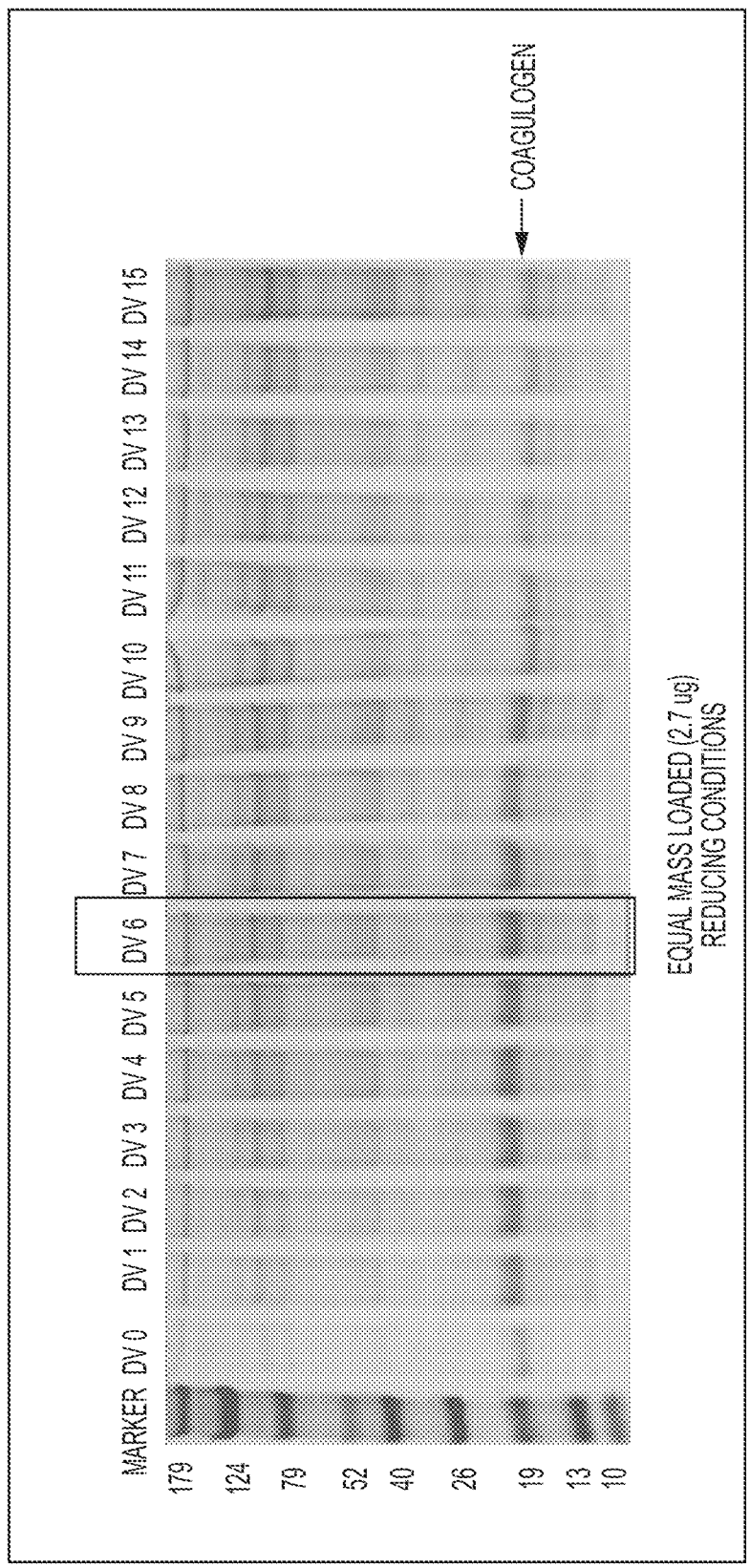
FIG. 11: SDS-PAGE gel of retentates from continuous tangential flow filtration after each diafiltration volume. The band at approximately 20 kDa indicates coagulogen.
Figure 12:
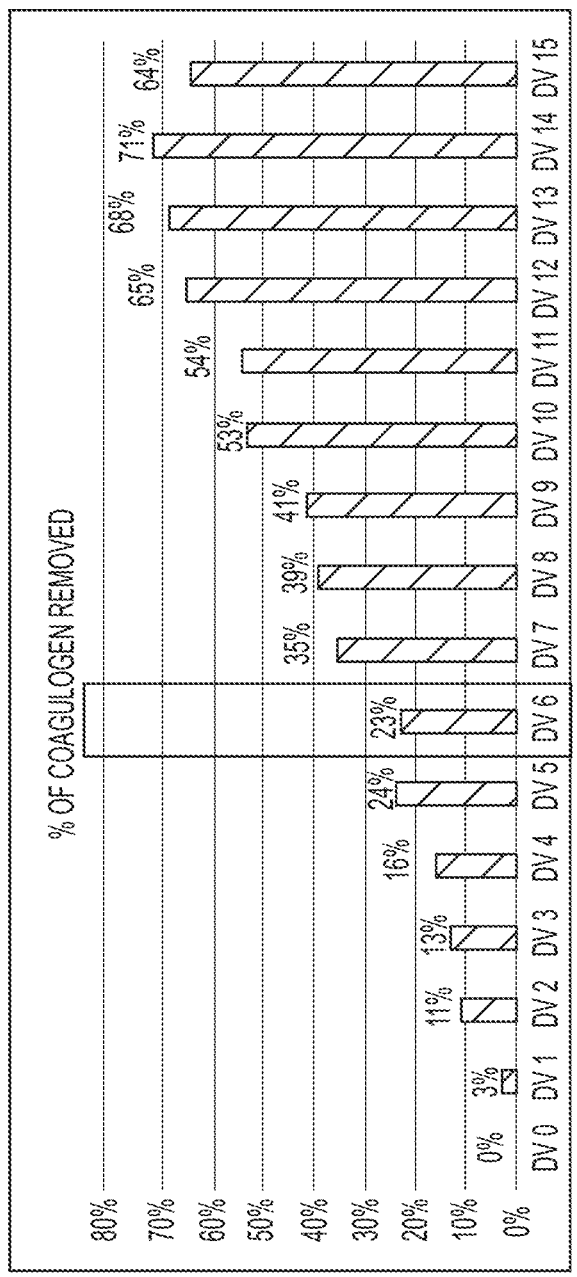
FIG. 12: Quantitation of the protein band at 20 kDa in the SDS-PAGE gel depicted in FIG. 11. The table (left) shows the total protein concentration in μg/μL of each retentate, and the percentage of the band at 20 kDa in the entire lane of the gel, calculated for each retentate obtained after the indicated number of diafiltration volumes.
Figure 13:
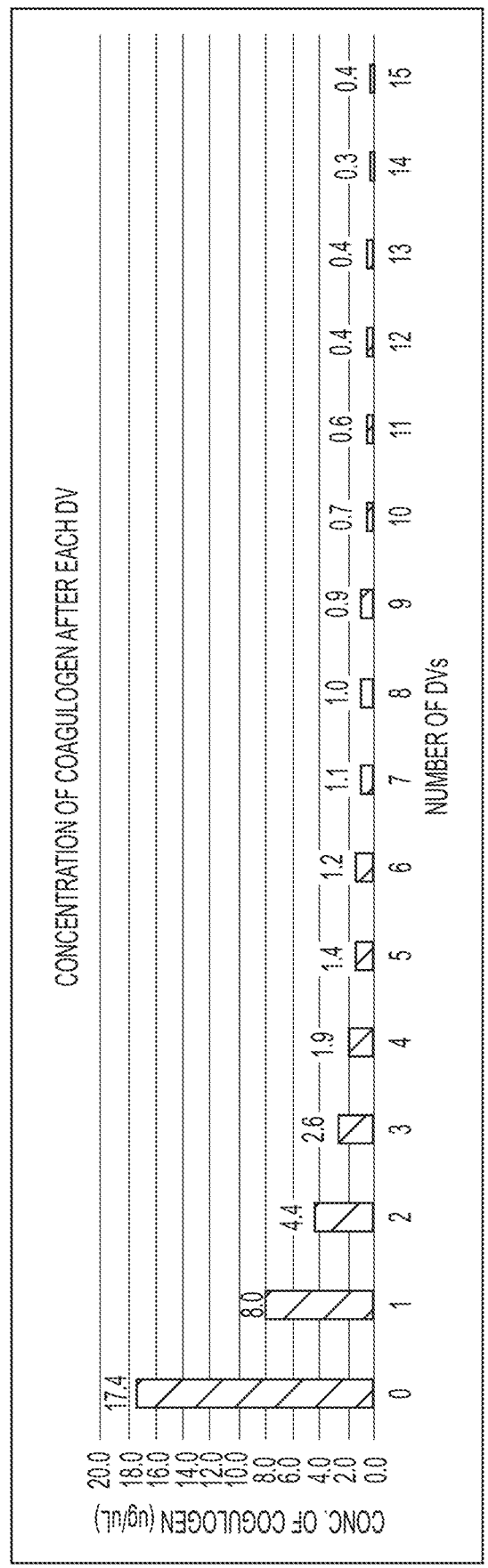
FIG. 13: Estimated concentration of coagulogen in μg/μL after each diafiltration volume of continuous tangential flow filtration.

SDS-PAGE analysis of the retentates from each of the DVs demonstrated that band density of the 20 kDa band (the approximate MW of coagulogen) decreased as more diafiltration volumes were used to wash the LAL. See, e.g., FIG. 11. Using band density from SDS-PAGE suggests coagulogen makes up about 37% of the total stained proteins in the unfiltered LAL, and that each diafiltration volume reduces the 20 kDa protein band. The concentration of total protein in each retentate collected at after each diafiltration volume was determined by measuring the absorbance at 280 nm. See, e.g., FIG. 12. Multiplying the percentage of each retentate sample that is made up of coagulogen using the data from the SDS-PAGE by the total concentration of protein, an estimate of the concentration of coagulogen in each retentate could be calculated. The concentration of coagulogen after each DV is represented in FIG. 13.

Example 5

Figure 15:
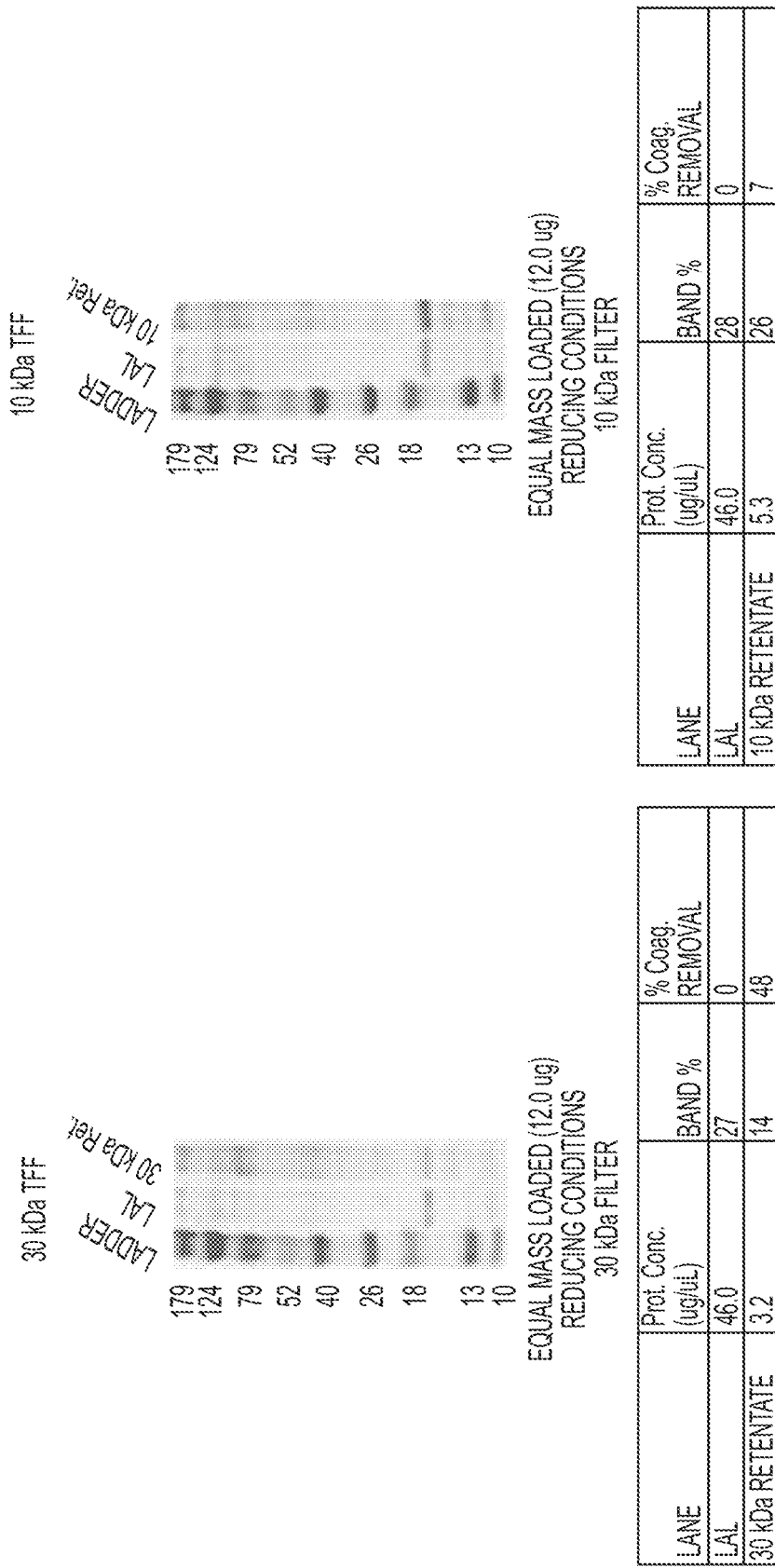
FIG. 15: Comparison of retentate from continuous tangential flow filtration using a 30 kDa filter (left) versus a 10 kDa filter (right), depicted by SDS-PAGE gel. The tables below each gel image indicate the percentage of coagulogen removal, as estimated by the band intensity in the gel.
Figure 16:
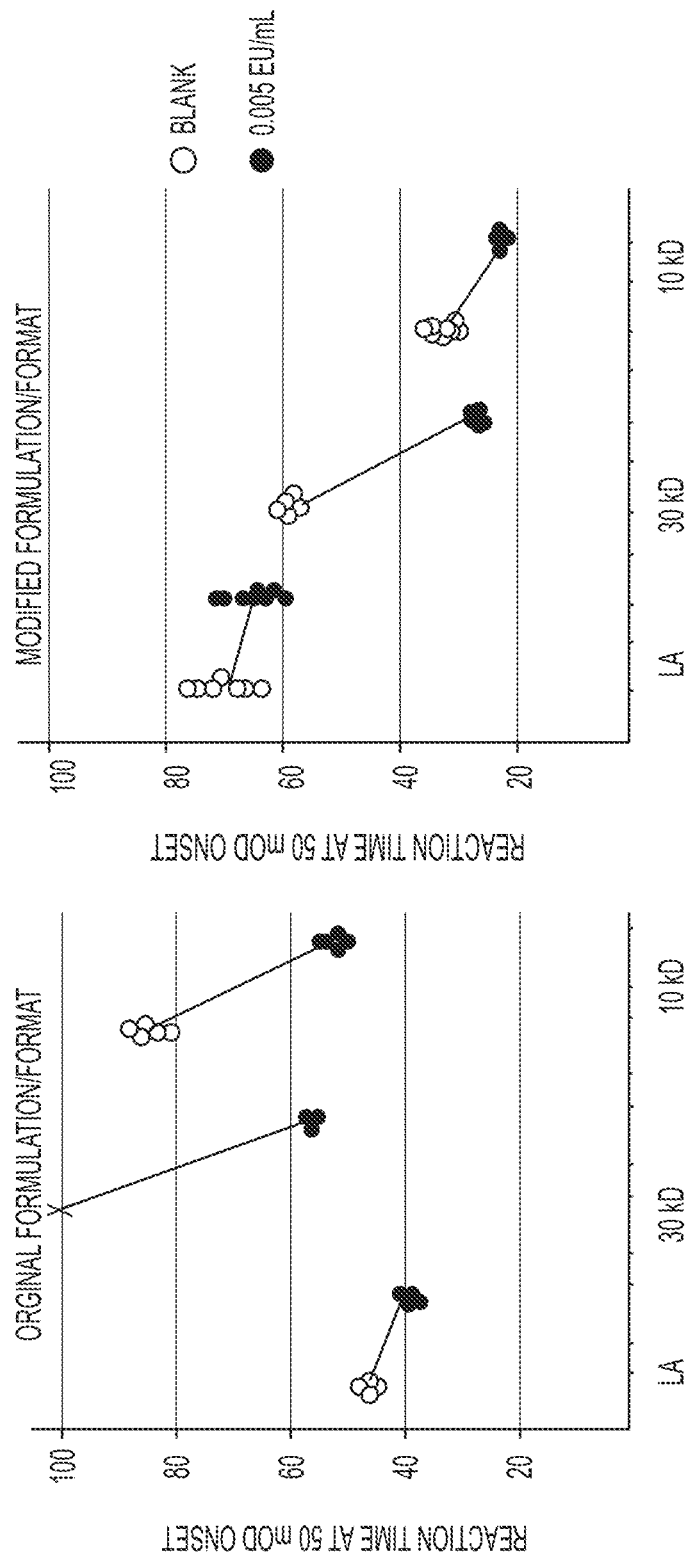
FIG. 16: Comparison of assay reaction times using unfiltered LAL, 30 kDa retentate, and 10 kDa retentate prepared using the original formulation and assay format (left) and modified formulation and assay format (right). The line indicates the difference in reaction times of the blank (non-solid) compared with 0.005 EU/mL (solid).

Numerous proteins are known to be present in unfiltered LAL compositions. A listing of some known proteins is presented in FIG. 14. Iwanaga S, et al., *Frontiers in Bioscience* 3. 973:973-984 (1998) Proteins with a molecular weight of less than 30 kDa are shaded. Investigations were made to determine whether the removal of other small molecular would contribute to enhanced performance. LAL compositions were subjected to continuous tangential flow filtration using either a 30 kDa filter, or a 10 kDa filter. As expected, SDS-PAGE demonstrated that coagulogen (approximately 20 kDa) was removed using the 30 kDa filter, but not the 10 kDa filter. See, FIG. 15. Continuous tangential flow filtration using a 30 kDa filter was shown to decrease reaction time relative to both the unfiltered LAL as well as the continuous tangential flow filtration using a 10 kDa filter. Continuous tangential flow filtration using a 30 kDa filter also improved separation between the blank and the 0.005 EU/mL samples relative to both the unfiltered LAL as well as the continuous tangential flow filtration using a 10 kDa filter.

Example 6

Figure 17:
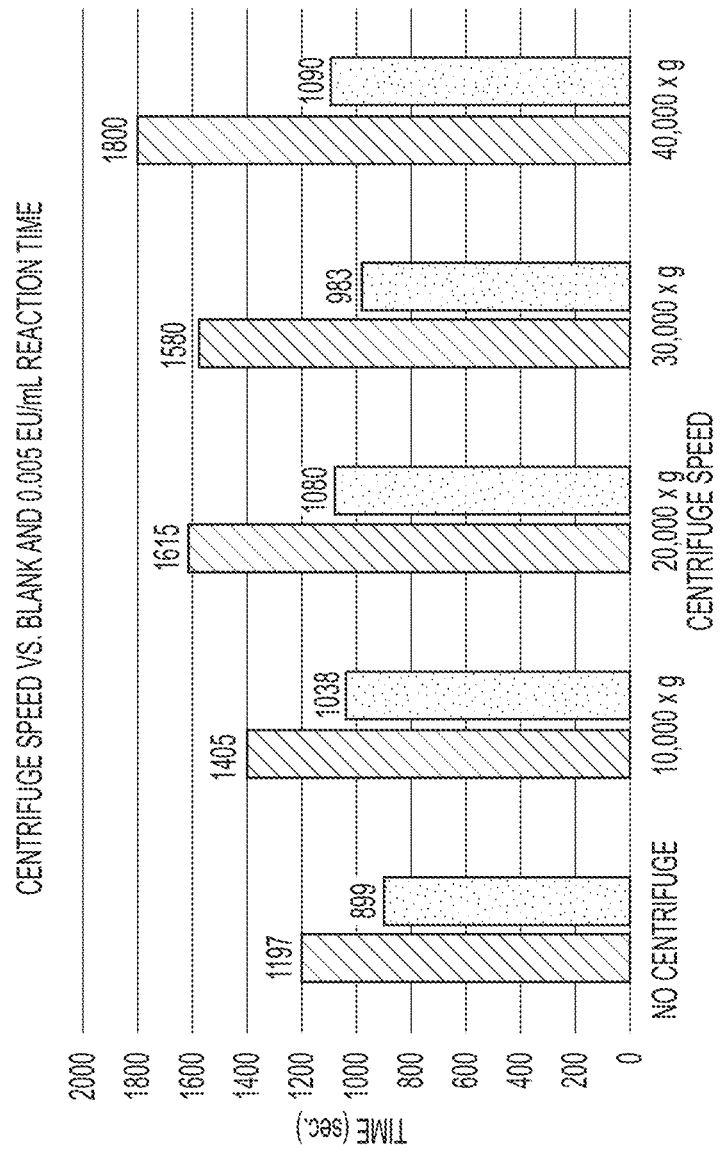
FIG. 17: Comparison of the effect of centrifugation speed on reaction time difference between blank and 0.005 EU/mL. Numbers above each bar indicate the reaction time.
Figures 18A, 18B:
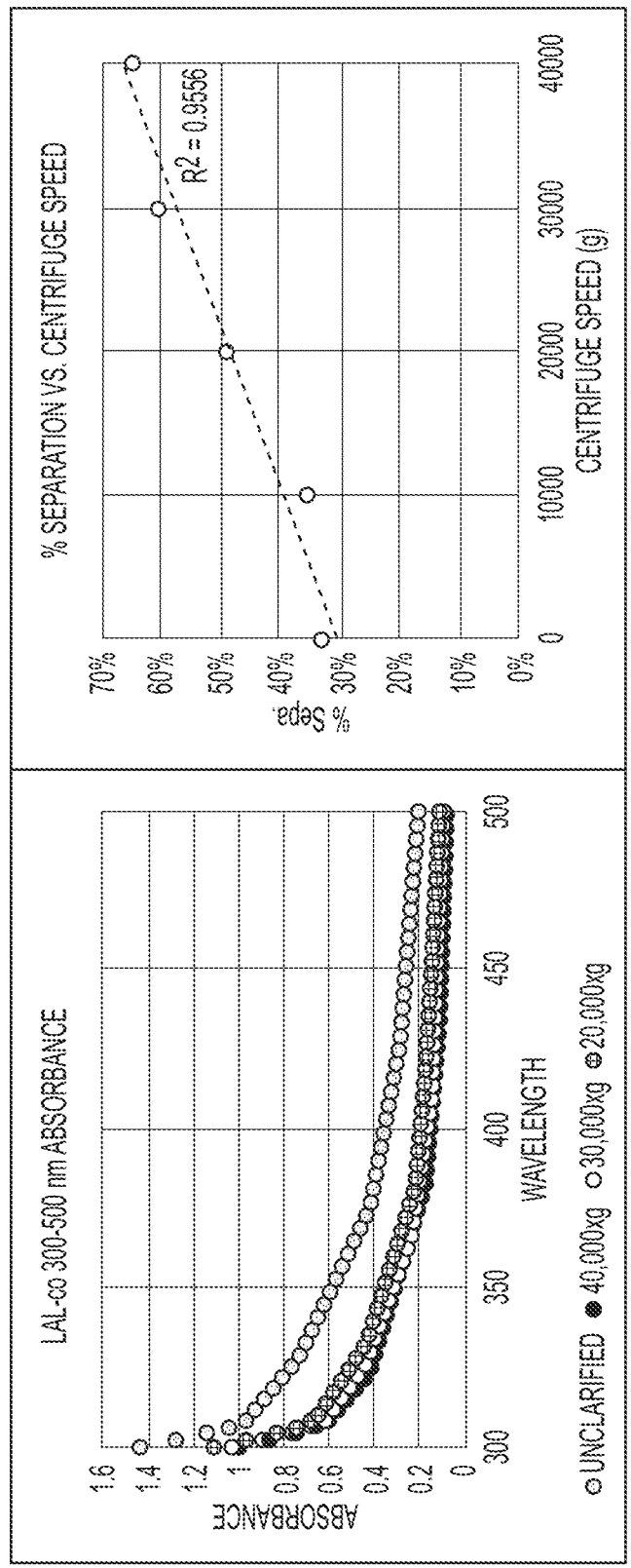
FIG. 18A: Comparison of optical density of unclarified 30 kDa retentate with 30 kDa retentate clarified by centrifugation at 40,000×g, 30,000×g, and 20,000×g, determined by absorbance at 300-500 nm.
FIG. 18B: Correlation of the difference in reaction time ("% Sepa.") between blank and 0.005 EU/mL with centrifugation rate, as depicted in FIG. 17.

The impact of centrifugation speed on the speed of reaction and separation was evaluated. LAL compositions were prepared and then centrifuged at either 10,000×g, 20,000×g, 30,000×g or 40,000×g for 30 minutes. The retentate was then tested for reaction time and separation using both a blank and a 0.005 EU/mL standard. Optical density of each of the retentates was also measured. The results are found in FIG. 17 and FIG. 18. Unclarified material has a higher optical density than centrifuged retentates. Also observed is a correlation between separation and the speed of centrifugation, wherein increasing the speed of centrifugation results in greater separation between the blank and the 0.005 EU/mL standard. Kinetic chromogenic assays performed to evaluate the performance of the clarified retentates utilizing an absorbance plate reader at 405 nM (Delta t (sec): 30, Delta mOD: 50) suggests that centrifugation is removing something that is contributing to substrate being cleaved independently of endotoxin, suggesting an additional benefit to the clarification step.

Example 7

Figure 19:
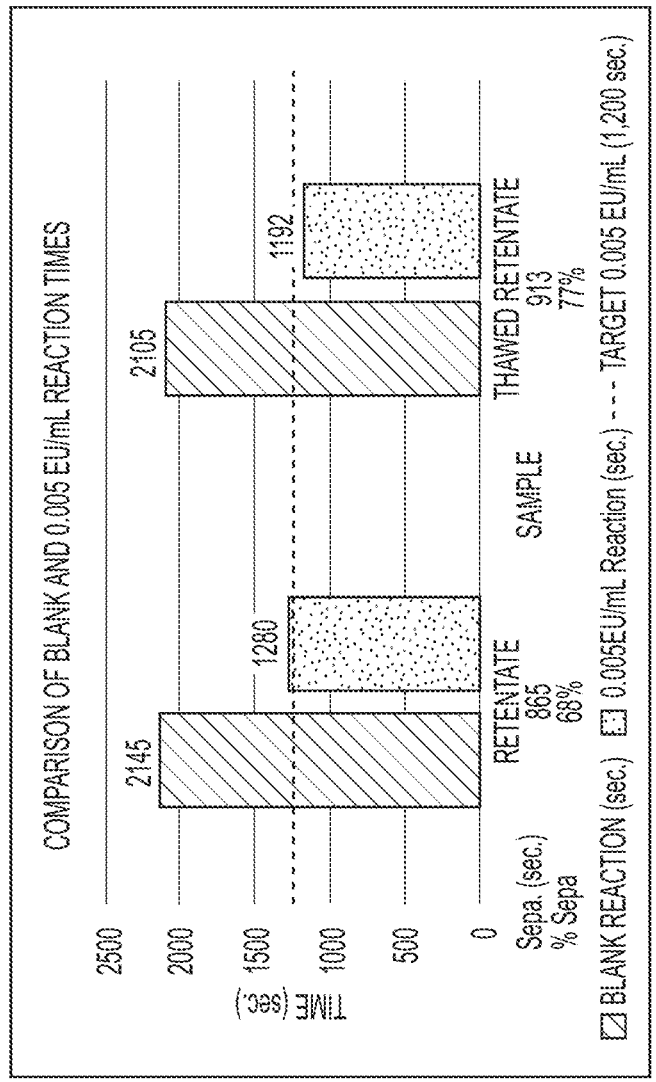
FIG. 19: Comparison of reaction time with blank or 0.005 EU/mL, using retentate that has not been frozen (left) or retentate that has been frozen and then thawed prior to the assay. The target reaction time for the 0.005 EU/mL retentate is 1200 seconds, indicated by the dotted line. Numbers below each set of bars represents the absolute ("Sepa. (sec.)") and percentage ("% Sepa.") difference between the reaction time of the blank and 0.005 EU/mL reaction time for the retentate. A positive difference indicates that the blank reacted slower than the 0.005 EU/mL. A negative difference indicates that the blank reacted faster than the 0.005 EU/mL.

The impact on performance caused by freezing and thawing the clarified LAL substantially free of coagulogen was investigated. The activity of the retentate produced by the method described herein (30 kDa continuous TFF, centrifuged at 30,000×g) was measured before freezing, and then after the retentate was frozen and thawed at room temperature. The results are presented in FIG. 19. This investigation suggested comparable performance before and after freezing/thawing.

It will be clear to one of ordinary skill in the relevant arts that other suitable modifications and adaptations to the methods and applications described herein can be made without departing from the scope of any of the embodiments. The previous examples are included herewith for purposes of illustration only and are not intended to be limiting.

It is to be understood that while certain embodiments have been illustrated and described herein, the claims are not to be limited to the specific forms or arrangement of parts described and shown. In the specification, there have been disclosed illustrative embodiments and, although specific terms are employed, they are used in a generic and descriptive sense only and not for purposes of limitation. Modifications and variations of the embodiments are possible in light of the above teachings. It is therefore to be understood that the embodiments may be practiced otherwise than as specifically described.

While various embodiments have been described above, they have been presented only as illustrations and examples of the present technology, and not by way of limitation. It will be apparent to persons skilled in the relevant art that various changes in form and detail can be made therein without departing from the spirit and scope of the present technology. Thus, the breadth and scope of the present technology should not be limited by any of the above-described embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A composition comprising clarified limulus amebocyte lysate (LAL) and a detergent, wherein the clarified LAL is LAL that has been (i) filtered using tangential flow filtration with a 20 kDa to 50 kDa filter to remove at least 60% (wt/wt) of its coagulogen such that it comprises less than 10% (wt/wt) of coagulogen relative to total protein in the LAL as measured by SDS-PAGE and protein stain, and then (ii) subjected to centrifugation.

2. The composition of claim 1, further comprising a buffer, wherein the composition comprises 30% to 60% (v/v) the clarified LAL.

3. The composition of claim 2, wherein the buffer is at a concentration of about 25 mM to about 50 mM.

4. The composition of claim 1, wherein the detergent is a zwitterionic detergent.

5. The composition of claim 1, wherein the detergent is at a concentration of about 0.002% to about 0.02%.

6. The composition claim 1, wherein the composition comprises about 50% the clarified LAL.

7. The composition of claim 1, further comprising a chromogenic substrate.

8. The composition of claim 7, wherein the chromogenic substrate is Ac-Ile-Glu-Ala-Arg-pNA.

9. The composition of claim 7, wherein the chromogenic substrate is at a concentration of about 0.11 mg/mL to about 0.77 mg/mL.

10. The composition of claim 1, wherein the composition is lyophilized, or wherein the composition is in an aqueous solution.

11. The composition of claim 1, wherein the clarified LAL comprises less than 5% (wt/wt) of coagulogen relative to total protein in the LAL as measured by SDS-PAGE and protein stain.

12. The composition of claim 1, wherein the clarified LAL comprises less than 5 µg/µL coagulogen.

13. The composition of claim 1, wherein the centrifugation is at greater than 1800 g for greater than 3 minutes.

14. The composition of claim 1, wherein the composition is capable of detecting endotoxin at a sensitivity of about 0.005 EU/mL or less.

15. A composition comprising
a. the composition of claim 1,
b. a buffer, and
c. a chromogenic substrate,
wherein the composition comprises 30% to 50% the clarified LAL (v/v) and 10% to 30% (v/v) the chromogenic substrate.

16. The compositions of claim 15, wherein the composition comprises 35% to 45% the clarified LAL and 15% to 25% the chromogenic substrate.

17. The composition of claim 15, wherein the composition comprises 40% the clarified LAL and 20% the chromogenic substrate.

18. A composition comprising clarified limulus amebocyte lysate (LAL) and a detergent, wherein the clarified LAL comprises less than 5% (wt/wt) of coagulogen relative to total protein in the LAL as measured by SDS-PAGE and protein stain, and wherein the clarified LAL is made by a method comprising:
a. obtaining a solution derived from lysed amebocytes from Limulus *polyphemus;*
b. combining the solution from (a) with a buffer;
c. subjecting the combination from (b) to continuous tangential flow filtration (TFF) using a 20 kDa to 50 kDa membrane filter to produce a retentate; and
d. centrifuging the retentate from (c) at greater than 20,000×g for greater than 25 minutes to produce a supernatant, wherein the supernatant is the clarified LAL.

19. A kit comprising:
a. a composition comprising clarified limulus amebocyte lysate (LAL) and a detergent, wherein the clarified LAL has been (i) filtered using tangential flow filtration with a 20 kDa to 50 kDa filter to remove at least 60% (wt/wt) of its coagulogen such that it comprises less than 10% (wt/wt) of coagulogen relative to total protein in the LAL as measured by SDS-PAGE and protein stain, and then (ii) subjected to centrifugation,
b. a chromogenic substrate; and
c. instructions for detecting an endotoxin using the composition and the chromogenic substrate.

20. The kit of claim 19, wherein the clarified LAL is lyophilized; or wherein the clarified LAL is in an aqueous solution.

* * * * *